US006228644B1

(12) United States Patent
Bogdanove et al.

(10) Patent No.: US 6,228,644 B1
(45) Date of Patent: May 8, 2001

(54) HYPERSENSITIVE RESPONSE ELICITOR FROM ERWINIA AMYLOVORA, ITS USE, AND ENCODING GENE

(75) Inventors: Adam J. Bogdanove; Jihyun Francis Kim, both of Ithaca, NY (US); Zhong-Min Wei, Kirkland, WA (US); Steven V. Beer, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/120,663

(22) Filed: Jul. 22, 1998

Related U.S. Application Data

(60) Provisional application No. 60/055,106, filed on Aug. 6, 1997.

(51) Int. Cl.[7] .............................. A01H 11/00; A01H 5/00; A01H 4/00; C12N 15/82; C12N 5/04

(52) U.S. Cl. .......................... 435/419; 435/69.1; 435/468; 435/410; 435/320; 435/252.3; 536/23.1; 536/23.7; 800/295; 800/298; 800/301; 800/305; 800/306; 800/307; 800/308; 800/309; 800/310; 800/311; 800/312; 800/313; 800/316; 800/317.4; 800/320; 800/323.2; 800/323.3

(58) Field of Search .................................... 435/69.1, 468, 435/410, 320, 419, 252.3; 536/23.1, 23.7; 800/278, 279, 295, 298, 301, 305, 306, 307, 308, 309, 310, 311, 312, 313, 316, 317.4, 320, 323.2, 323.3

(56) References Cited

U.S. PATENT DOCUMENTS

| | | | |
|---|---|---|---|
| 4,569,841 | 2/1986 | Liu | 424/93.4 |
| 4,597,972 | 7/1986 | Taylor | 426/36 |
| 4,601,842 | 7/1986 | Caple et al. | 252/70 |
| 4,740,593 | 4/1988 | Gonzalez et al. | 422/1 |
| 4,851,223 | 7/1989 | Sampson | 424/711 |
| 4,886,825 | 12/1989 | Ruess et al. | 514/383 |
| 4,931,581 | 6/1990 | Schurter et al. | 560/18 |
| 5,057,422 | 10/1991 | Bol et al. | 424/93.47 |
| 5,061,490 | 10/1991 | Paau et al. | 424/93.47 |
| 5,135,910 | 8/1992 | Blackburn et al. | 514/2 |
| 5,173,403 | 12/1992 | Tang | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 504/117 |
| 5,260,271 | 11/1993 | Blackburn et al. | 514/2 |
| 5,348,743 | 9/1994 | Ryals et al. | 424/94.61 |
| 5,494,684 | 2/1996 | Cohen | 424/523 |
| 5,523,311 | 6/1996 | Schurter et al. | 514/361 |
| 5,550,228 | 8/1996 | Godiard et al. | 800/298 |
| 5,552,527 | 9/1996 | Godiard et al. | 530/379 |
| 5,650,387 | 7/1997 | Wei et al. | 514/2 |
| 5,708,139 | 1/1998 | Collmer et al. | 530/350 |
| 5,850,015 | 12/1998 | Bauer et al. | 800/279 |
| 6,001,959 | 12/1999 | Bauer et al. | 530/300 |

FOREIGN PATENT DOCUMENTS

| | | |
|---|---|---|
| 0 612 848 A3 | 8/1994 | (EP) . |
| WO 93/23532 | 11/1993 | (WO) . |
| WO 94/01546 | 1/1994 | (WO) . |
| WO 94/26782 | 11/1994 | (WO) . |
| WO 95/19443 | 7/1995 | (WO) . |
| WO 96/39802 | 12/1996 | (WO) . |
| WO 98/15547 | 4/1998 | (WO) . |
| WO 98/24297 | 6/1998 | (WO) . |
| WO 98/32844 | 7/1998 | (WO) . |
| WO 98/37752 | 9/1998 | (WO) . |
| WO 98/54214 | 12/1998 | (WO) . |
| WO 99/07206 | 2/1999 | (WO) . |
| WO 99/07207 | 2/1999 | (WO) . |

OTHER PUBLICATIONS

Alfano et al., "Analysis of the Role of the *Pseudomonas syringae* pv. *syringae* HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19(4):715–728 (1996).

Lorang et al., "Characterization of avrE from *Pseudomonas syringae* pv. Tomato: A hrp–Linked Avirulence Locus Consisting Of at Least Two Transcriptional Units," *MPMI* 8(1):49–57 (1995).

Malamy et al., Salicylic Acid and Plant Disease Resistance, *The Plant Journal*, 2(5):643–654 (1992).

McGurl et al., "Structure, Expression, and Antisense Inhibition of the Systemin Precursor Gene," *Science*, 255:1570–1573 (1992).

Schulte et al., "Expression of the *Xanthomonas campestris* pv. Vesicatoria hrp Gene Cluster, Which Determines Pathogenicity and Hypersensitivity on Pepper and Tomato, Is Plant Inducible," *Journal of Bacteriology*, 174:815–823 (1992).

(List continued on next page.)

*Primary Examiner*—Lynette R. F. Smith
*Assistant Examiner*—Ousama M-Fuiz Zaghmout
(74) *Attorney, Agent, or Firm*—Nixon Peabody LLP

(57) ABSTRACT

The present invention is directed to an isolated protein or polypeptide which elicits a hypersensitive response in plants as well as an isolated DNA molecule which encodes the hypersensitive response eliciting protein or polypeptide. This isolated protein or polypeptide and the isolated DNA molecule can used to impart disease resistance to plants, to enhance plant growth, and/or to control insects on plants. This can be achieved by applying the hypersensitive response elicitor protein or polypeptide in a non-infectious form to plants or plant seeds under conditions effective to impart disease resistance, to enhance plant growth, and/or to control insects on plants or plants grown from the plant seeds. Alternatively, transgenic plants or plant seeds transformed with a DNA molecule encoding a hypersensitive response elicitor protein or polypeptide can be provided and the transgenic plants or plants resulting from the transgenic plant seeds are grown under conditions effective to impart disease resistance, to enhance plant growth, and/or to control insects on plants or plants grown from the plant seeds.

16 Claims, 5 Drawing Sheets-

OTHER PUBLICATIONS

Wu et al., "Disease Resistance Conferred by Expression of a Gene Encoding $H_2O_2$–Generating Glucose Oxidase in Transgenic Potato Plants," *The Plant Cell*, 7:1357–1368 (1995).

Yu, "Elicitins from Phytophthora and Basic Resistance in Tobacco," *Proc. Natl. Acad. Sci. USA*, 92:4088–4094 (1995).

Nissinen et al., "*Clavibacter michiganensis* Subsp. *sepedonicus* Elicits a Hypersensitive Response in Tobacco and Secretes Hypersensitive Response–Inducing Protein," *Phytopathology*, 87:678–684 (1997) (Abstract only).

Kloepper et al., "Enhanced Plant Growth by Siderophores Produced by Plant Growth–promoting Rhizobacteria," *Nature* 286:885–886 (1980).

Collmer et al., "*Erwinia chyrsanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. glycines," Seventh International Symposium on Molecular Plant Microbe Interactions, Abstract No. 244 (Jun. 1994).

Preston et al., "The HrpZ Proteins of *Pseudomonas syringae* pvs. *syringae, glycinea*, and tomato are Encoded by an Operon Containing *Yersinia ysc* Homologs and Elicit the Hypersensitive Response in Tomato but not Soybean," *Mol. Plant–Microbe Interact.*, 8(5):717–32 (1995).

Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Incompatible Pseudomonas spp. by Blasticidin S, Streptomycin or Elevated Temperature," *Physiological Plant Pathology*, 18:325–37 (1981).

Lerner, R.A., "Tapping the Immunological Repertoire to Produce Antibodies of Predetermined Specificity," *Nature*, 299:592–96 (1982).

Staskawicz et al., "Cloned Avirulence Gene of *Pseudomonas Syringae* pv. *glycinea* Determines Race–specific Incompatibility on *Glycine max* (L.) Merr.," *Proc. Natl. Acad. Sci. USA*, 81:6024–28 (1984).

Bauer et al., "*Erwinia chrysanthemi* $Harpin_{Ech}$: An Elicitor of the Hypersensitive Response that Contributes to Soft–Rot Pathogenesis," *MPMI*, 8(4):484–91 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, an Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Microbio.*, 192:79–98 (1994).

Arlat et al., "PopA1, A Protein Which Induces a Hypersensitivity–Like Response on Specific Protein Petunia Genotypes, is Secreted via the Hrp Pathway of *Pseudomonas solanacearum,*" *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas solanacearum* To Colony Appearance on a Tetrazolium Medium," *Phytopathology*, 44:693–95 (1954).

Winstead et al., "Inoculation Techniques For Evaluating Resistance to *Pseudomonas solanacearum,*" *Phytopathology*, 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant and Soil*, 77:103–13 (1984).

Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).

Atkinson et al., "The Hypersensitive Reaction of Tobacco to *Pseudomonas syringae* pv. *pisi,*" *Plant Physiol.*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease*, 72(1):42–6 (1988).

Kloepper et al., "Enhanced Plant Growth by Siderophores Produced by Plant Growth–Promoting Rhizobacteria," *Nature*, 286:885–86 (1980).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed), Plenum, NY, 155–64 (1986).

Kloepper et al., "Relationships of in vitro Antibiosis of Plant Growth–Promoting Rhizobacteria to Plant Growth and the Displacement of Root Microflora," *Phytopathology*, 71(10):1020–24 (1981).

Kloepper et al., "Effects of Rhizosphere Colonization by Plant Growth–Promoting Rhizobacteria on Potato Plant Development and Yield," *Phytophathology*, 70(11):1078–82 (1980).

Kloepper et al., "Plant Growth Promotion Mediated by Rhizosphere Bacterial Colonizers," In: *The Rhizosphere and Plant Growth*, —315–32, Keister et al. (eds), pp. 315–326 (1991).

Lifshitz et al., "Growth Promotion of Canola (rapeseed) Seedlings by a Strain of *Pseudomonas putida* Under Gnotobiotic Conditions," Conditions, *Micribiol.* 33:390–95 (1987).

Liu et al., "Induction of Systemic Resistance in Cucumber Against Bacterial Angular Leaf Spot by Plant Growth–Promoting Rhizobacteria," *Phytopathology*, 85(8):843–47 (1995).

Loper et al., "Influence of Bacterial Sources of Indole–3–acetic Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512–22 (1986).

Bauer et al., "Cloning of a Gene from *Erwinia Amylovora* Involved in Induction of Hypersensitivity and Pathogenicity," *Plant Pathogenic Bacteria*, Proceedings of the Sixth International Conference on Plant Pathogenic Bacteria, Maryland, pp. 425–429 (1987).

Wei et al., "Induction of Systemic Resistance of Cucumber to *Colletotrichum orbiculare* by Select Strains of Plant Growth–Promoting Rhizobacteria," *Phytopathology*, 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186.

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection," *Science*, 250:1002–04 (1990).

Dean et al., "Immunisation Against Disease: The Plant Fights Back," pp. 383–411.

Cameron et al., "Biologically Induced Systemic Acquired Resistance in *Arabidopsis thaliana," The Plant Journal*, 5(5):715–25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Microbiol.*, 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli," Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Bonnet, et al., "Induction de nécroses foliaires, de protéines b et de résistance dans les interactions tabac Phytophthora," *Agronomie*, 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).

Kang et al., "Control of Tomato Mosaic Disease by Interference of an Attenuated Virus," *Res. Rept. RDA* (*Hort.*), 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya, Biologiya* 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).

Shields, R., "Towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748–56 (1988).

Ricci, et al., "Differential Production of Parasiticein, an Elicitor of Necrosis and Resistance in Tobacco, by Isolates of *Phytophthora parasitica," Plant Pathology*, 41:298–307 (1992).

Honée, et al., "Molecular Characterization of the Interaction Between the Fungal Pathogen *Cladosporium fulvum* and Tomato," *Advances in Molecular Genetics of Plant–Microbe Interactions*, 3:199–206 (1994).

Keller, et al., "Responses of Tobacco to Elicitins, Proteins From *Phytophthora spp.* Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi hrp* Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).

Steinberger et al., "Creation and Complementation of Pathogenicity Mutants of *Erwinia amylovora," Molecular Plant–Microbe Interactions*, 1(3):135–44 (1988).

Beer et al., "The Hypersensitive Response is Elicited by *Escherichia coli* Containing a Cluster of Pathogenicity Genes from *Erwinia amylovora," Phytopathology*, 79(10):1156 (Abstract 169) (1989).

Hiatt et al., "Production of Antibodies in Transgenic Plants," *Nature*, 342:76–8 (1989).
Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).
Huang et al., "Isolation and Purification of a Factor from *Pseudomonas solanacearum* That Induces a Hypersensitive–like Response in Potato Cells," *Molecular Plant–Microbe Interactions*, 2(3):132–38 (1989).
James et al., "Genetic Transformation of Apple (*Malus pumila* Mill.) Using a Disarmed Ti–binary Vector," *Plant Cell Reports*, 7:658–61 (1989).
Laby et al., "Cloning and Preliminary Characterization of an hrp Gene Cluster of *Erwinia amylovora,*" *Phytopathology*, 79(10):1211 (Abstract 607) (1989).
Dow et al., "Extracellular Proteases from *Xanthomonas campestris* pv. Campestris, the Black Rot Pathogen," *Applied and Environmental Microbiology*, 56(10):2994–98 (1990).
Walters et al., "Gene for Pathogenicity and Ability to Cause the Hypersensitive Reaction Cloned from *Erwinia amylovora,*" *Physiological and Molecular Plant Pathology*, 36:509–21 (1990).
Wu et al., "Cloning, Genetic Organization, and Characterization of a Structural Gene Encoding Bacillopeptidase F from *Bacillus subtilis,*" *The Journal of Biological Chemistry*, 265(12):6845–50 (1990).
Bauer et al., "Further Characterization of an hrp Gene Cluster of *Erwinia amylovora,*" *Molecular Plant–Microbe Interactions*, 4(5):493–99 (1991).
Beer et al., "The hrp Gene Cluster of *Erwinia amylovora,*" *Advances in Molecular Genetics of Plant–Microbe Interactions*, 1:53–60 (1991).
Benvenuto et al., "'Phytoantibodies': A General Vector for the Expression of Immunoglobulin Domains in Transgenic Plants," *Plant Molecular Biology*, 17:865–74 (1991).
Milat et al., "Physiological and Structural Changes in Tobacco Leaves Treated with Cryptogein, a Proteinaceous Elicitor from *Phytophthora cryptogea,*" *Phytopathology*, 81(11):1364–68 (1991).
Ruberti et al., "A Novel Class of Plant Proteins Containing a Homeodomain with a Closely Linked Leucine Zipper Motif," *The EMBO Journal*, 10(7):1787–91 (1991).
Quigley et al., "Nucleotide Sequence and Expression of a Novel Glycine–Rich Protein Gene from *Arabidopsis thaliana,*" *Plant Molecular Biology*, 17:949–52 (1991).
van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–9 (1991).
Waldmann, T.A., "Monoclonal Antibodies in Diagnosis and Therapy," *Science*, 252:1657–62 (1991).
Willis et al., "hrp Genes of Phytopathogenic Bacteria," *Molecular Plant–Microbe Interactions*, 4:(2) 132–38 (1991).
Beer et al., "Are Harpins Universal Elicitors of the Hypersensitive Response of Phytopathogenic Bacteria?," *Advances in Molecular Genetics of Plant–Microbe Interactions*, 2:281–86 (1992).
Laby et al., "Hybridization and Functional Complementation of the hrp Gene Cluster from *Erwinia amylovora* Strain Ea321 with DNA of Other Bacteria," *Molecular Plant–Microbe Interactions*, 5(5):412–19 (1992).
Sandhu, "Protein Engineering of Antibodies," *Crit. Rev. in Biotech.*, 12(5/6):437–62 (1992).
Wei et al., "Harpin, Elicitor of the Hypersensitive Response Produced by the Plant Pathogen *Erwinia amylovora,*" *Science*, 257:85–8 (1992).
He et al., "*Pseudomonas syringae* pv. *syringae* Harpin$_{Pss}$: A Protein that is Secreted via the Hrp Pathway and Elicits the Hypersensitive Response in Plants," *Cell*, 73:1255–66 (1993).
Bonas, U., "Bacterial Home Goal by Harpins," *Trends in Microbiology*, 2:1–2 (1994).
Boccara, et al., "Plant Defense Elicitor Protein Produced by *Erwinia chrysanthemi,*" *Mechanisms of Plant Defense Responses*, p. 166 (1993).
Qui et al., "Treatment of Tomato Seed with Harpin Enhances Germination and Growth and Induces Resistance to *Ralstonia solanacearum,*" *Phytopathology*, 87:6, S80 (1997).
Burr et al., "Increased Potato Yields by Treatment of Seedpieces with Specific Strains of *Pseudomonas fluorescens* and *P. putida,*" *Phytopathology*, 68:1377–1383 (1978).
Ricci et al., "Proteinaceous Elicitors of Plant Defense Responses," B. Fritig eds., *Mechanisms of Plant Defense Responses*, Netherlands, pp. 121–130 (1993).
Keen et al., "Syringolide Elicitors Specified By Avirulence Gene D Alleles In *Pseudomonas syringae,*" *Advances in Molecular Genetics of Plant–Microbe Interactions*, 3:41–48 (1994).
Klessig et al., "The Salicylic Acid Signal In Plants," *Plant Molecular Biology*, 26:1439–1458 (1994).
Bogdanove et al., "Unified Nomenclature For Broadly Conserved hrp Genes of Phytopathogenic Bacteria," *Molecular Microbiology*, 20(3):681–683 (1996).
Bonnet et al., "Acquired Resistance Triggered By Elicitins In Tobacco and Other Plants," *European Journal of Plant Pathology*, 102:181–192 (1996).
Cui et al., "The RsmA$^-$ Mutants of *Erwinia carotovora* subsp. *carotovora* Strain Ecc71 Overexpress hrpN$_{Ecc}$ and Elicit a Hypersensitive Reaction–like Response in Tobacco Leaves," *Molecular Plant–Microbe Interactions*, 9(7):565–573 (1996).
Gopalan et al., "Bacterial Genes Involved in the Elicitation of Hypersensitive Response and Pathogenesis," *Plant Disease*, 80(6):604–610 (1996).
Hoffland et al., "Comparison of Systemic Resistance Induced by Avirulent and Nonpathogenic Pseudomonas Species," *Phytopathology*, 86(7):757–762 (1996).
Ryals et al., "Systemic Acquired Resistance," *The Plant Cell*, 8:1809–1819 (1996).
Wei et al., "Induced Systemic Resistance to Cucumber Dieseases and Increased Plant Growth by Plant Growth–Promoting Rhizobacteria Under Field Conditions," *Phytopathology*, 86:221–224 (1996).
Wengelnik et al., "Expression and Localization of HrpA1, a Protein of *Xanthomonas campestris* pv. *vesicatoria* Essential for Pathogenicity and Induction of the Hypersensitive Reaction," *Journal of Bacteriology*, 178:1061–1069 (1996).
Inbar et al., "Elicitors of Plant Defensive Systems Reduce Insect Densities and Disease Incidence," *Journal of Chemical Ecology*, 24(1):135–149 (1998).
Jin et al., "A Truncated Fragment of Harpin$_{Pss}$ Induces Systemic Resistance To *Xanthomonas campetris* pv. *oryzae* In Rice," *Physiological and Molecular Plant Pathology*, 51:243–257 (1997).

HYPERSENSITIVE RESPONSE ELICITOR FROM ERWINIA AMYLOVORA, ITS USE, AND ENCODING GENE

This application claims benefit of U.S. Provisional Patent Application Ser. No. 60/055,106, filed Aug. 6, 1997.

FIELD OF THE INVENTION

The present invention relates to a hypersensitive response elicitor from *Erwinia amylovora*, its use, and encoding gene.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response ("HR") is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes*, Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals-Molecular and Cellular Mechanisms*, J. L. Dangl, ed. Springer-Verlag, Berlin (1994)). Several hrp genes encode components of a protein secretion pathway similar to one used by Yersinia, Shigella, and Salmonella spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae*, and *P. solanacearum*, hrp genes have been shown to control the production and secretion of glycine-rich, protein elicitors of the hypersensitive response (He, S. Y., et al. "Pseudomonas Syringae pv. Syringae Harpin$_{Pss}$: a Protein that is Secreted via the Hrp Pathway and Elicits the Hypersensitive Response in Plants," *Cell* 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopAl, a Protein Which Induces a Hypersensitive-like Response on Specific Petunia Genotypes, is Secreted via the Hrp Pathway of *Pseudomonas solanacearum," EMBO J.* 13:543–553 (1994)).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora," Science* 257:85–88 (1992)). Mutations in the encoding hrpN gene revealed that the hypersensitive response elicitor is required for *E. amylovora* to elicit a hypersensitive response in nonhost tobacco leaves and incite disease symptoms in highly susceptible pear fruit. The *P. solanacearum* GMI1000 PopAl protein has similar physical properties and also elicits the hypersensitive response in leaves of tobacco, which is not a host of that strain (Arlat, et al. "PopAl, a Protein Which Induces a Hypersensitive-like Response on Specific Petunia Genotypes, is Secreted via the Hrp Pathway of *Pseudomonas solanacearum," EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated and their encoding genes have been cloned and sequenced. These include: *Erwinia chrysanthemi* (Bauer, et. al., "*Erwinia chrysanthemi* Harpin$_{Ech}$: Soft-Rot Pathogenesis," *MPMI* 8(4): 484–91 (1995)); *Erwinia carotovora* (Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," *8th Int'l. Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae* pv. *syringae* (WO 94/26782 to Cornell Research Foundation, Inc.).

The present invention is a further advance in the effort to identify, clone, and sequence hypersensitive response elicitor proteins or polypeptides from plant pathogens.

SUMMARY OF THE INVENTION

The present invention is directed to an isolated protein or polypeptide which elicits a hypersensitive response in plants as well as an isolated DNA molecule which encodes the hypersensitive response eliciting protein or polypeptide.

The hypersensitive response eliciting protein or polypeptide can be used to impart disease resistance to plants, to enhance plant growth, and/or to control insects. This involves applying the hypersensitive response elicitor protein or polypeptide in a non-infectious form to plants or plant seeds under conditions effective to impart disease resistance, to enhance plant growth, and/or to control insects on plants or plants grown from the plant seeds.

As an alternative to applying the hypersensitive response elicitor protein or polypeptide to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding a hypersensitive response elicitor protein or polypeptide and growing the plant under conditions effective to impart disease resistance, to enhance plant growth, and/or to control insects in the plants or plants grown from the plant seeds. Alternatively, a transgenic plant seed transformed with the DNA molecule encoding a hypersensitive response elicitor protein or polypeptide can be provided and planted in soil. A plant is then propagated under conditions effective to impart disease resistance, to enhance plant growth, and/or to control insects on plants or plants grown from the plant seeds.

BRIEF DESCRIPTION OF THE DRAWINGS

FIG. 1A shows the dsp/hrp gene cluster of *E. amylovora* in pCPP430. Operon names and types of proteins encoded are indicated at the top. B, BamHI; E, EcoRI; H, HindIII. Half-arrows indicate internal promoters without similarity to the hrp box consensus. FIG. 1B shows the region downstream of hrpN containing the dspE operon. Circles mark deletion mutations and representative transposon insertions: black, non-pathogenic and $HR^+$ (i.e. hypersensitive response eliciting) or HR reduced (dsp); gray, reduced virulence and HR; white, wild-type. T104 lies within the area marked by the dashed double arrow. K, Tn5miniKm; P, Tn5phoA; T, Tn10tet$^r$; Δ, deletion mutation. The gray box is A/T-rich DNA. FIG. 1C shows the clones and subclones of the dspE operon. Plasmid designations are indicated at the left, and vector-borne promoters at the right. Restriction sites used for subdloning not shown above are shown in parentheses. A "+" aligned with a circle representing a mutation in B indicates that the subclone complements that mutation. FIG. 1D shows the avrE locus (transcription units III and IV) of *P. syringae* pv. tomato DC3000 in pCPP2357. Percent amino acid identity of the predicted proteins AvrE and AvrF to DspE and DspF, respectively, are indicated. Black rectangles are transcriptional terminators (inverted repeats). Complementation of mutations shown in FIG. 1B are depicted as in FIG. 1C, above.

FIG. 3A shows immature pear fruit 4 days after inoculation with (left to right) strains Ea321, Ea321dspEΔ1554, or Ea321dspEΔ1554 harboring the 5' half of dspE on pCPP1237. FIG. 3B shows Norchief soybean leaf 24 hr after infiltration with (1) Ea321, (2) Ea321dspEΔ1554, (3) Ea321hrpN::Tn5 (Wei, et al., *Science,* 257:85–88 (1992), which is hereby incorporated by reference), and (4) Ea321hrpL::Tn5 (Wei, et al., *J. Bacteriol.,* 177:6201–10 (1995), which is hereby incorporated by reference). FIG. 3C shows a tobacco leaf 48 hr after infiltration with parallel dilution series of suspensions of strains (left) Ea321 and (right) Ea321dspEΔ1554. The concentrations infiltrated (top to bottom) are $1\times10^{10}$, $1\times10^{9}$, $5\times10^{8}$, and $5\times10^{7}$ cfu/ml. FIG. 3D is like FIG. 3C except the more virulent strain Ea273 and corresponding mutant Ea273dspEΔ1554 were used, and concentrations ranged from $5\times10^{9}$ to $5\times10^{5}$ cfu/ml in log increments.

FIG. 5C shows pear halves inoculated with (left to right) Ea321, Ea321dspEΔ1521(pCPP2357, containing the avrE locus), or Ea321dspEΔ1521(pCPP2357avrE::Tn5uidA) and photographed after seven days. Although symptoms are greatly reduced relative to wild type, necrosis is apparent around and drops of ooze can be seen within the well of the fruit inoculated with the dspE strain carrying the intact avrE locus. The fruit inoculated with the dspE strain carrying a disrupted clone of avrE is symptomless.

DETAILED DESCRIPTION OF THE INVENTION

Figures 1A, 1B, 1C, 1D:
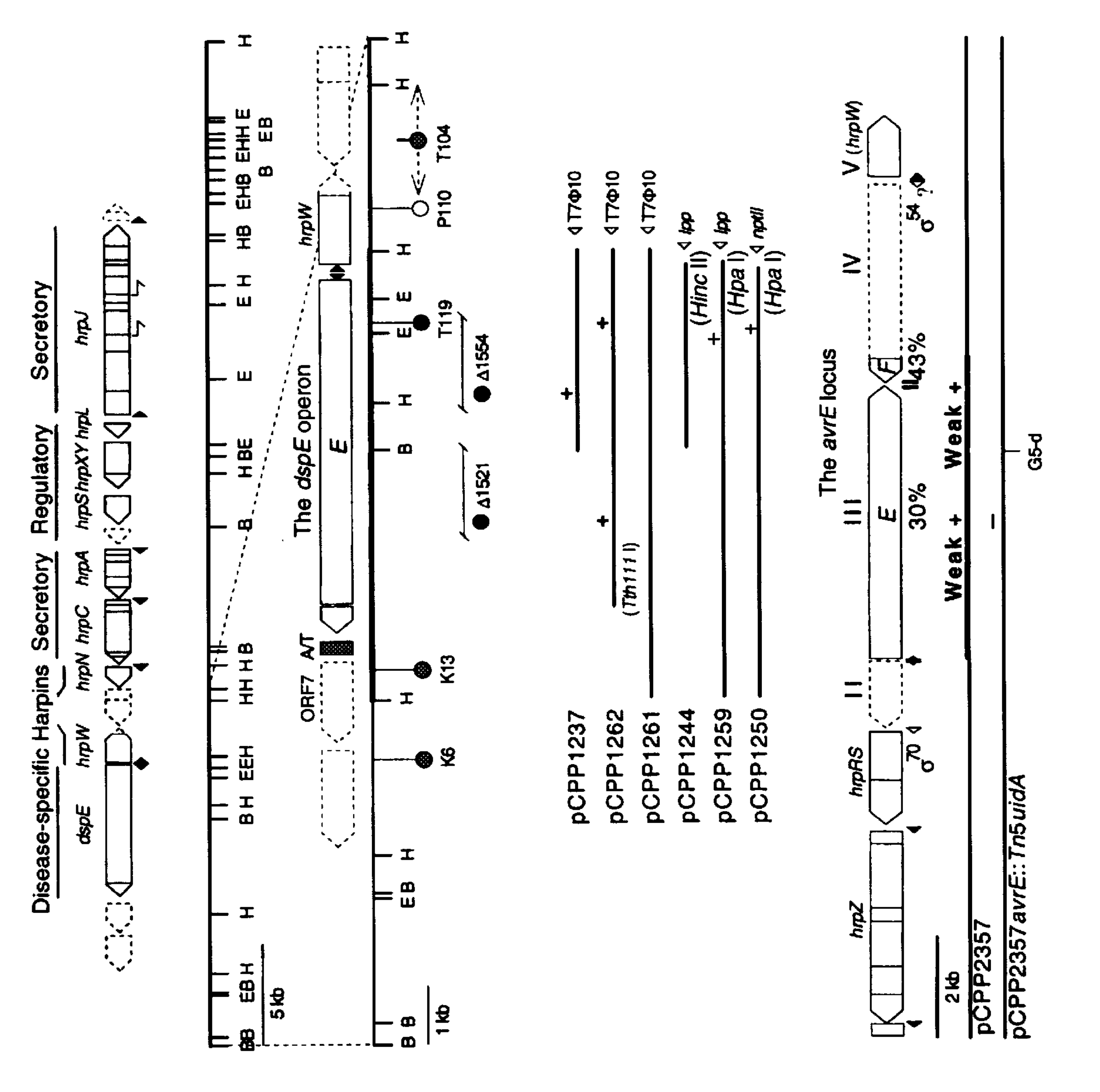
FIGS. 1A–D show mutagenesis, complementation and heterologous expression constructs, and homology with and complementation of mutants by the avrE locus of *P. syringae* for the dspE operon of *E. amylovora*. Dashed boxes are uncharacterized ORFs; a filled triangle indicates a hrp (i.e. hypersensitive response elicitor encoding gene); box is a regulatory sequence that preceeds many hrp genes; and an open triangle indicates another promoter. Thick lines delineate the DNA for which sequence was accessioned.

The present invention relates to an isolated DNA molecule having a nucleotide sequence of SEQ. ID. No. 1 as follows:

```
ATGGAATTAA AATCACTGGG AACTGAACAC AAGGCGGCAG TACACACAGC GGCGCACAAC    60
CCTGTGGGGC ATGGTGTTGC CTTACAGCAG GGCAGCAGCA GCAGCAGCCC GCAAAATGCC   120
GCTGCATCAT TGGCGGCAGA AGGCAAAAAT CGTGGGAAAA TGCCGAGAAT TCACCAGCCA   180
TCTACTGCGG CTGATGGTAT CAGCGCTGCT CACCAGCAAA AGAAATCCTT CAGTCTCAGG   240
GGCTGTTTGG GGACGAAAAA ATTTTCCAGA TCGGCACCGC AGGGCCAGCC AGGTACCACC   300
CACAGCAAAG GGGCAACATT GCGCGATCTG CTGGCGCGGG ACGACGGCGA AACGCAGCAT   360
GAGGCGGCCG CGCCAGATGC GGCGCGTTTG ACCCGTTCGG GCGGCGTCAA ACGCCGCAAT   420
ATGGACGACA TGGCCGGGCG GCCAATGGTG AAAGGTGGCA GCGGCGAAGA TAAGGTACCA   480
ACGCAGCAAA AACGGCATCA GCTGAACAAT TTTGGCCAGA TGCGCCAAAC GATGTTGAGC   540
AAAATGGCTC ACCCGGCTTC AGCCAACGCC GGCGATCGCC TGCAGCATTC ACCGCCGCAC   600
ATCCCGGGTA GCCACCACGA AATCAAGGAA GAACCGGTTG GCTCCACCAG CAAGGCAACA   660
ACGGCCCACG CAGACAGAGT GGAAATCGCT CAGGAAGATG ACGACAGCGA ATTCCAGCAA   720
CTGCATCAAC AGCGGCTGGC GCGCGAACGG GAAAATCCAC CGCAGCCGCC CAAACTCGGC   780
GTTGCCACAC CGATTAGCGC CAGGTTTCAG CCCAAACTGA CTGCGGTTGC GGAAAGCGTC   840
CTTGAGGGGA CAGATACCAC GCAGTCACCC CTTAAGCCGC AATCAATGCT GAAAGGAAGT   900
GGAGCCGGGG TAACGCCGCT GGCGGTAACG CTGGATAAAG GCAAGTTGCA GCTGGCACCG   960
GATAATCCAC CCGCGCTCAA TACGTTGTTG AAGCAGACAT TGGGTAAAGA CACCCAGCAC  1020
TATCTGGCGC ACCATGCCAG CAGCGACGGT AGCCAGCATC TGCTGCTGGA CAACAAAGGC  1080
CACCTGTTTG ATATCAAAAG CACCGCCACC AGCTATAGCG TGCTGCACAA CAGCCACCCC  1140
GGTGAGATAA AGGGCAAGCT GGCGCAGGCG GGTACTGGCT CCGTCAGCGT AGACGGTAAA  1200
AGCGGCAAGA TCTCGCTGGG GAGCGGTACG CAAAGTCACA ACAAAACAAT GCTAAGCCAA  1260
CCGGGGGAAG CGCACCGTTC CTTATTAACC GGCATTTGGC AGCATCCTGC TGGCGCAGCG  1320
CGGCCGCAGG GCGAGTCAAT CCGCCTGCAT GACGACAAAA TTCATATCCT GCATCCGGAG  1380
CTGGGCGTAT GGCAATCTGC GGATAAAGAT ACCCACAGCC AGCTGTCTCG CCAGGCAGAC  1440
GGTAAGCTCT ATGCGCTGAA AGACAACCGT ACCCTGCAAA ACCTCTCCGA TAATAAATCC  1500
TCAGAAAAGC TGGTCGATAA AATCAAATCG TATTCCGTTG ATCAGCGGGG GCAGGTGGCG  1560
ATCCTGACGG ATACTCCCGG CCGCCATAAG ATGAGTATTA TGCCCTCGCT GGATGCTTCC  1620
CCGGAGAGCC ATATTTCCCT CAGCCTGCAT TTTGCCGATG CCCACCAGGG GTTATTGCAC  1680
GGGAAGTCGG AGCTTGAGGC ACAATCTGTC GCGATCAGCC ATGGGCGACT GGTTGTGGCC  1740
GATAGCGAAG GCAAGCTGTT TAGCGCCGCC ATTCCGAAGC AAGGGGATGG AAACGAACTG  1800
AAAATGAAAG CCATGCCTCA GCATGCGCTC GATGAACATT TTGGTCATGA CCACCAGATT  1860
TCTGGATTTT TCCATGACGA CCACGGCCAG CTTAATGCGC TGGTGAAAAA TAACTTCAGG  1920
CAGCAGCATG CCTGCCCGTT GGGTAACGAT CATCAGTTTC ACCCCGGCTG GAACCTGACT  1980
GATGCGCTGG TTATCGACAA TCAGCTGGGG CTGCATCATA CCAATCCTGA ACCGCATGAG  2040
ATTCTTGATA TGGGGCATTT AGGCAGCCTG GCGTTACAGG AGGGCAAGCT TCACTATTTT  2100
GACCAGCTGA CCAAAGGGTG GACTGGCGCG GAGTCAGATT GTAAGCAGCT GAAAAAAGGC  2160
CTGGATGGAG CAGCTTATCT ACTGAAAGAC GGTGAAGTGA AACGCCTGAA TATTAATCAG  2220
AGCACCTCCT CTATCAAGCA CGGAACGGAA AACGTTTTTT CGCTGCCGCA TGTGCGCAAT  2280
AAACCGGAGC CGGGAGATGC CCTGCAAGGG CTGAATAAAG ACGATAAGGC CCAGGCCATG  2340
GCGGTGATTG GGTAAATAA ATACCTGGCG CTGACGGAAA AAGGGGACAT TCGCTCCTTC   2400
```

-continued

```
CAGATAAAAC CCGGCACCCA GCAGTTGGAG CGGCCGGCAC AAACTCTCAG CCGCGAAGGT  2460
ATCAGCGGCG AACTGAAAGA CATTCATGTC GACCACAAGC AGAACCTGTA TGCCTTGACC  2520
CACGAGGGAG AGGTGTTTCA TCAGCCGCGT GAAGCCTGGC AGAATGGTGC CGAAAGCAGC  2580
AGCTGGCACA AACTGGCGTT GCCACAGAGT GAAAGTAAGC TAAAAAGTCT GGACATGAGC  2640
CATGAGCACA AACCGATTGC CACCTTTGAA GACGGTAGCC AGCATCAGCT GAAGGCTGGC  2700
GGCTGGCACG CCTATGCGGC ACCTGAACGC GGGCCGCTGG CGGTGGGTAC CAGCGGTTCA  2760
CAAACCGTCT TTAACCGACT AATGCAGGGG GTGAAAGGCA AGGTGATCCC AGGCAGCGGG  2820
TTGACGGTTA AGCTCTCGGC TCAGACGGGG GGAATGACCG GCGCCGAAGG GCGCAAGGTC  2880
AGCAGTAAAT TTTCCGAAAG GATCCGCGCC TATGCGTTCA ACCCAACAAT GTCCACGCCG  2940
CGACCGATTA AAAATGCTGC TTATGCCACA CAGCACGGCT GGCAGGGGCG TGAGGGGTTG  3000
AAGCCGTTGT ACGAGATGCA GGGAGCGCTG ATTAAACAAC TGGATGCGCA TAACGTTCGT  3060
CATAACGCGC CACAGCCAGA TTTGCAGAGC AAACTGGAAA CTCTGGATTT AGGCGAACAT  3120
GGCGCAGAAT TGCTTAACGA CATGAAGCGC TTCCGCGACG AACTGGAGCA GAGTGCAACC  3180
CGTTCGGTGA CCGTTTTAGG TCAACATCAG GGAGTGCTAA AAGCAACGG TGAAATCAAT  3240
AGCGAATTTA AGCCATCGCC CGGCAAGGCG TTGGTCCAGA GCTTTAACGT CAATCGCTCT  3300
GGTCAGGATC TAAGCAAGTC ACTGCAACAG GCAGTACATG CCACGCCGCC ATCCGCAGAG  3360
AGTAAACTGC AATCCATGCT GGGGCACTTT GTCAGTGCCG GGGTGGATAT GAGTCATCAG  3420
AAGGGCGAGA TCCCGCTGGG CCGCCAGCGC GATCCGAATG ATAAAACCGC ACTGACCAAA  3480
TCGCGTTTAA TTTTAGATAC CGTGACCATC GGTGAACTGC ATGAACTGGC CGATAAGGCG  3540
AAACTGGTAT CTGACCATAA ACCCGATGCC GATCAGATAA AACAGCTGCG CCAGCAGTTC  3600
GATACGCTGC GTGAAAAGCG GTATGAGAGC AATCCGGTGA AGCATTACAC CGATATGGGC  3660
TTCACCCATA ATAAGGCGCT GGAAGCAAAC TATGATGCGG TCAAAGCCTT TATCAATGCC  3720
TTTAAGAAAG AGCACCACGG CGTCAATCTG ACCACGCGTA CCGTACTGGA ATCACAGGGC  3780
AGTGCGGAGC TGGCGAAGAA GCTCAAGAAT ACGCTGTTGT CCCTGGACAG TGGTGAAAGT  3840
ATGAGCTTCA GCCGGTCATA TGGCGGGGGC GTCAGCACTG TCTTTGTGCC TACCCTTAGC  3900
AAGAAGGTGC CAGTTCCGGT GATCCCCGGA GCCGGCATCA CGCTGGATCG CGCCTATAAC  3960
CTGAGCTTCA GTCGTACCAG CGGCGGATTG AACGTCAGTT TTGGCCGCGA CGGCGGGGTG  4020
AGTGGTAACA TCATGGTCGC TACCGGCCAT GATGTGATGC CCTATATGAC CGGTAAGAAA  4080
ACCAGTGCAG GTAACGCCAG TGACTGGTTG AGCGCAAAAC ATAAAATCAG CCCGGACTTG  4140
CGTATCGGCG CTGCTGTGAG TGGCACCCTG CAAGGAACGC TACAAAACAG CCTGAAGTTT  4200
AAGCTGACAG AGGATGAGCT GCCTGGCTTT ATCCATGGCT TGACGCATGG CACGTTGACC  4260
CCGGCAGAAC TGTTGCAAAA GGGGATCGAA CATCAGATGA AGCAGGGCAG CAAACTGACG  4320
TTTAGCGTCG ATACCTCGGC AAATCTGGAT CTGCGTGCCG GTATCAATCT GAACGAAGAC  4380
GGCAGTAAAC CAAATGGTGT CACTGCCCGT GTTTCTGCCG GGCTAAGTGC ATCGGCAAAC  4440
CTGGCCGCCG GCTCGCGTGA ACGCAGCACC ACCTCTGGCC AGTTTGGCAG CACGACTTCG  4500
GCCAGCAATA ACCGCCCAAC CTTCCTCAAC GGGGTCGGCG CGGGTGCTAA CCTGACGGCT  4560
GCTTTAGGGG TTGCCCATTC ATCTACGCAT GAAGGGAAAC CGGTCGGGAT CTTCCCGGCA  4620
TTTACCTCGA CCAATGTTTC GGCAGCGCTG GCGCTGGATA ACCGTACCTC ACAGAGTATC  4680
AGCCTGGAAT TGAAGCGCGC GGAGCCGGTG ACCAGCAACG ATATCAGCGA GTTGACCTCC  4740
ACGCTGGGAA AACACTTTAA GGATAGCGCC ACAACGAAGA TGCTTGCCGC TCTCAAAGAG  4800
```

-continued

```
TTAGATGACG CTAAGCCCGC TGAACAACTG CATATTTTAC AGCAGCATTT CAGTGCAAAA  4860

GATGTCGTCG GTGATGAACG CTACGAGGCG GTGCGCAACC TGAAAAAACT GGTGATACGT  4920

CAACAGGCTG CGGACAGCCA CAGCATGGAA TTAGGATCTG CCAGTCACAG CACGACCTAC  4960

AATAATCTGT CGAGAATAAA TAATGACGGC ATTGTCGAGC TGCTACACAA ACATTTCGAT  5040

GCGGCATTAC CAGCAAGCAG TGCCAAACGT CTTGGTGAAA TGATGAATAA CGATCCGGCA  5100

CTGAAAGATA TTATTAAGCA GCTGCAAAGT ACGCCGTTCA GCAGCGCCAG CGTGTCGATG  5160

GAGCTGAAAG ATGGTCTGCG TGAGCAGACG GAAAAAGCAA TACTGGACGG TAAGGTCGGT  5220

CGTGAAGAAG TGGGAGTACT TTTCCAGGAT CGTAACAACT TGCGTGTTAA ATCGGTCAGC  5280

GTCAGTCAGT CCGTCAGCAA AAGCGAAGGC TTCAATACCC CAGCGCTGTT ACTGGGGACG  5340

AGCAACAGCG CTGCTATGAG CATGGAGCGC AACATCGGAA CCATTAATTT TAAATACGGC  5400

CAGGATCAGA ACACCCCACG GCGATTTACC CTGGAGGGTG GAATAGCTCA GGCTAATCCG  5460

CAGGTCGCAT CTGCGCTTAC TGATTTGAAG AAGGAAGGGC TGGAAATGAA GAGCTAA     5517
```

This DNA molecule is known as the dspE gene. This isolated DNA molecule of the present invention encodes a protein or polypeptide which elicits a plant pathogen's hypersensitive response having an amino acid sequence of SEQ. ID. No. 2 as follows:

```
Met Glu Leu Lys Ser Leu Gly Thr Glu His Lys Ala Ala Val His Thr
1               5                   10                  15

Ala Ala His Asn Pro Val Gly His Gly Val Ala Leu Gln Gln Gly Ser
            20                  25                  30

Ser Ser Ser Ser Pro Gln Asn Ala Ala Ala Ser Leu Ala Ala Glu Gly
        35                  40                  45

Lys Asn Arg Gly Lys Met Pro Arg Ile His Gln Pro Ser Thr Ala Ala
    50                  55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
    210                 215                 220

Asp Arg Val Glu Ile Ala Gln Glu Asp Asp Ser Glu Phe Gln Gln
225                 230                 235                 240

Leu His Gln Gln Arg Leu Ala Arg Glu Arg Glu Asn Pro Pro Gln Pro
                245                 250                 255
```

-continued

```
Pro Lys Leu Gly Val Ala Thr Pro Ile Ser Ala Arg Phe Gln Pro Lys
            260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
    290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
            340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
    370                 375                 380

Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
                405                 410                 415

Met Leu Ser Gln Pro Gly Glu Ala His Arg Ser Leu Leu Thr Gly Ile
            420                 425                 430

Trp Gln His Pro Ala Gly Ala Ala Arg Pro Gln Gly Glu Ser Ile Arg
        435                 440                 445

Leu His Asp Asp Lys Ile His Ile Leu His Pro Glu Leu Gly Val Trp
    450                 455                 460

Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
        515                 520                 525

His Lys Met Ser Ile Met Pro Ser Leu Asp Ala Ser Pro Glu Ser His
    530                 535                 540

Ile Ser Leu Ser Leu His Phe Ala Asp Als His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
        595                 600                 605

Ala Leu Asp Glu His Phe Gly His Asp His Gln Ile Ser Gly Phe Phe
    610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Gly Pro His Glu Ile Leu Asp Met Gly His Leu Gly
        675                 680                 685
```

-continued

```
Ser Leu Ala Leu Gln Glu Gly Lys Leu His Tyr Phe Asp Gln Leu Thr
    690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
            725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
        755                 760                 765

Gln Gly Leu Asn Lys Asp Asp Lys Ala Gln Ala Met Ala Val Ile Gly
    770                 775                 780

Val Asn Lys Tyr Leu Ala Leu Thr Glu Lys Gly Asp Ile Arg Ser Phe
785                 790                 795                 800

Gln Ile Lys Pro Gly Thr Gln Gln Leu Glu arg Pro Ala Gln Thr Leu
            805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
        835                 840                 845

Pro Arg Glu Ala Trp Gln Asn Gly Ala Glu Ser Ser Ser Trp His Lys
    850                 855                 860

Leu Ala Leu Pro Gln Ser Glu Ser Lys Leu Lys Ser Leu Asp Met Ser
865                 870                 875                 880

His Glu His Lys Pro Ile Ala Thr Phe Glu Asp Gly Ser Gln His Gln
            885                 890                 895

Leu Lys Ala Gly Gly Trp His Ala Tyr Ala Ala Pro Glu Arg Gly Pro
            900                 905                 910

Leu Ala Val Gly thr Ser Gly Ser Gln Thr Val Phe Asn Arg Leu Met
        915                 920                 925

Gln Gly Val Lys Gly Lys Val Ile Pro Gly Ser Gly Leu Thr Val Lys
    930                 935                 940

Leu Ser Ala Gln Thr Gly Gly Met Thr Gly Ala Glu Gly Arg Lys Val
945                 950                 955                 960

Ser Ser Lys Phe Ser Glu Arg Ile Arg Ala Tyr Ala Phe Asn Pro Thr
            965                 970                 975

Met Ser Thr Pro Arg Pro Ile Lys Asn Ala Ala Tyr Ala Thr Gln His
            980                 985                 990

Gly Trp Gln Gly Arg Glu Gly Leu Lys Pro Leu Tyr Glu Met Gln Gly
        995                 1000                1005

Ala Leu Ile Lys Gln Leu Asp Ala His Asn Val Arg His Asn Ala Pro
    1010                1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
            1045                1050                1055

Gln Ser Ala Thr Arg Ser Val Thr Val Leu Gly Gln His Gln Gly Val
            1060                1065                1070

Leu Lys Ser Asn Gly Glu Ile Asn Ser Glu Phe Pys Pro Ser Pro Gly
        1075                1080                1085

Lys Ala Leu Val Gln Ser Phe Asn Val Asn Arg Ser Gly Gln Asp Leu
    1090                1095                1100

Ser Lys Ser Leu Gln Gln Ala Val His Ala Thr Pro Pro Ser Ala Glu
```

-continued

```
1105                1110                1115                1120

Ser Lys Leu Gln Ser Met Leu Gly His Phe Val Ser Ala Gly Val Asp
                1125                1130                1135

Met Ser His Gln Lys Gly Glu Ile Pro Leu Gly Arg Gln Arg Asp Pro
            1140                1145                1150

Asn Asp Lys Thr Ala Leu Thr Lys Ser Arg Leu Ile Leu Asp Thr Val
        1155                1160                1165

Thr Ile Gly Glu Leu His Glu Leu Ala Asp Lys Ala Lys Leu Val Ser
    1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
                1205                1210                1215

Thr Asp Met Gly Phe Thr His Asn Lys Ala Leu Glu Ala Asn Tyr Asp
            1220                1225                1230

Ala Val Lys Ala Phe Ile Asn Ala Phe Lys Lys Glu His His Gly Val
        1235                1240                1245

Asn Leu Thr Thr Arg Thr Val Leu Glu Ser Gln Gly Ser Ala Glu Leu
    1250                1255                1260

Ala Lys Lys Leu Lys Asn Thr Leu Leu Ser Leu Asp Ser Gly Glu Ser
1265                1270                1275                1280

Met Ser Phe Ser Arg Ser Tyr Gly Gly Gly Val Ser Thr Val Phe Val
                1285                1290                1295

Pro Thr Leu Ser Lys Lys Val Pro Val Pro Val Ile Pro Gly Ala Gly
            1300                1305                1310

Ile Thr Leu Asp Arg Ala Tyr Asn Ley Ser Phe Ser Arg Thr Ser Gly
        1315                1320                1325

Gly Leu Asn Val Ser Phe Gly Arg Asp Gly Gly Val Ser Gly Asn Ile
    1330                1335                1340

Met Val Ala Thr Gly His Asp Val Met Pro Tyr Met Thr Gly Lys Lys
1345                1350                1355                1360

Thr Ser Ala Gly Asn Ala Ser Asp Trp Leu Ser Ala Lys His Lys Ile
                1365                1370                1375

Ser Pro Asp Leu Arg Ile Gly Ala Ala Val Ser Gly Thr Leu Gln Gly
            1380                1385                1390

Thr Leu Gln Asn Ser Leu Lys Phe Lys Leu Thr Glu Asp Glu Leu Pro
        1395                1400                1405

Gly Phe Ile His Gly Leu Thr His Gly Thr Leu Thr Pro Ala Glu Leu
    1410                1415                1420

Leu Gln Lys Gly Ile Glu His Gln Met Lys Gln Gly Ser Lys Leu Thr
1425                1430                1435                1440

Phe Ser Val Asp Thr Ser ala Asn Leu Asp Leu Arg Ala Gly Ile Asn
                1445                1450                1455

Leu Asn Glu Asp Gly Ser Lys Pro Asn Gly Val Thr Ala Arg Val Ser
            1460                1465                1470

Ala Gly Leu Ser Ala Ser Ala Asn Leu Ala Ala Gly Ser Arg Glu Arg
        1475                1480                1485

Ser Thr Thr Ser Gly Gln Phe Gly Ser Thr Thr Ser Ala Ser Asn Asn
    1490                1495                1500

Arg Pro Thr Phe Leu Asn Gly Val Gly Ala Gly Ala Asn Leu Thr Ala
1505                1510                1515                1520

Ala Leu Gly Val Ala His Ser Ser Thr His Glu Gly Lys Pro Val Gly
                1525                1530                1535
```

-continued

```
Ile Phe Pro Ala Phe Thr Ser Thr Asn Val Ser ala Ala Leu Ala Leu
            1540                1545                1550

Asp Asn Arg Thr Ser Gln Ser Ile Ser Leu Glu Leu Lys Arg Ala Glu
        1555                1560                1565

Pro Val Thr Ser Asn Asp Ile Ser Glu Leu Thr Ser Thr Leu Gly Lys
    1570                1575                1580

His Phe Lys Asp Ser Ala Thr Thr Lys Met Leu Ala Ala Leu Lys Glu
1585                1590                1595                1600

Leu Asp Asp Ala Lys Pro Ala Glu Gln Leu His Ile Leu Gln Gln His
                1605                1610                1615

Phe Ser Ala Lys Asp Val Val Gly Asp Glu Arg Tyr Glu Ala Val Arg
            1620                1625                1630

Asn Leu Lys Lus Leu Val Ile Arg Gln Gln Ala Ala Asp Ser His Ser
        1635                1640                1645

Met Glu Leu Gly Ser Ala Ser His Ser Thr Thr Tyr Asn Asn Leu Ser
    1650                1655                1660

Arg Ile Asn Asn Asp Gly Ile Val Glu Leu Leu His Lys His Phe Asp
1665                1670                1675                1680

Ala Ala Leu Pro Ala Ser Ser Ala Lys Arg Leu Gly Glu Met Met Asn
                1685                1690                1695

Asn Asp Pro Ala Leu Lys Asp Ile Ile Lys Gln Leu Gln Ser Thr Pro
            1700                1705                1710

Phe Ser Ser Ala Ser Val Ser Met Glu Leu Lys Asp Gly Leu Arg Glu
        1715                1720                1725

Gln Thr Glu Lys Ala Ile Leu Asp Gly Lys Val Gly Arg Glu Glu Val
    1730                1735                1740

Gly Val Leu Phe Gln Asp Arg Asn Asn Leu Arg Val Lys Ser Val Ser
1745                1750                1755                1760

Val Ser Gln Ser Val Ser Lus Ser Glu Gly Phe Asn Thr Pro Ala Leu
                1765                1770                1775

Leu Leu Gly Thr Ser Asn Ser Ala Ala Met Ser Met Glu Arg Asn Ile
            1780                1785                1790

Gly Thr Ile Asn Phe Lys Tyr Gly Gln Asp Gln Asn Thr Pro Arg Arg
        1795                1800                1805

Phe Thr Leu Glu Gly Gly Ile Ala Gln Ala Asn Pro Gln Val Ala Ser
    1810                1815                1820

Ala Leu Thr Asp Leu Lys Lys Glu Gly Leu Glu Met Lys Ser
1825                1830                1835
```

This protein or polypeptide is about 198 kDa and has a pI of 8.98.

The present invention relates to an isolated DNA molecule having a nucleotide sequence of SEQ. ID. No. 3 as follows:

```
ATGACATCGT CACAGCAGCG GGTTGAAAGG TTTTTACAGT ATTTCTCCGC CGGGTGTAAA   60

ACGCCCATAC ATCTGAAAGA CGGGGTGTGC GCCCTGTATA ACGAACAAGA TGAGGAGGCG  120

GCGGTGCTGG AAGTACCGCA ACACAGCGAC AGCCTGTTAC TACACTGCCG AATCATTGAG  180

GCTGACCCAC AAACTTCAAT AACCCTGTAT TCGATGCTAT TACAGCTGAA TTTTGAAATG  240

GCGGCCATGC GCGGCTGTTG GCTGGCGCTG GATGAACTGC ACAACGTGCG TTTATGTTTT  300

CAGCAGTCGC TGGAGCATCT GGATGAAGCA AGTTTTAGCG ATATCGTTAG CGGCTTCATC  360

GAACATGCGG CAGAAGTGCG TGAGTATATA GCGCAATTAG ACGAGAGTAG CGCGGCATAA  420
```

This is known as the dspF gene. This isolated DNA molecule of the present invention encodes a hypersensitive response elicitor protein or polypeptide having an amino acid sequence of SEQ. ID. No. 4 as follows:

```
Met Thr Ser Ser Gln Gln Arg Val Glu Arg Phe Leu Gln Tyr Phe Ser
1               5                   10                  15

Ala Gly Cys Lys Thr Pro Ile His Leu Lys Asp Gly Val Cys Ala Leu
            20                  25                  30

Tyr Asn Glu Gln Asp Glu Glu Ala Ala Val Leu Glu Val Pro Gln His
        35                  40                  45

Ser Asp Ser Leu Leu Leu His Cys Arg Ile Ile Glu Ala Asp Pro Gln
    50                  55                  60

Thr Ser Ile Thr Leu Tyr Ser Met Leu Leu Gln leu Asn Phe Glu Met
65                  70                  75                  80

Ala Ala Met Arg Gly Cys Trp Leu Ala Leu Asp Glu Leu His Asn Val
                85                  90                  95

Arg Leu Cys Phe Gln Gln Ser Leu Glu His Leu Asp Glu Ala Ser Phe
            100                 105                 110

Ser Asp Ile Val Ser Gly Phe Ile Glu His Ala Ala Glu Val Arg Glu
        115                 120                 125

Tyr Ile Ala Gln Leu Asp Glu Ser Ser Ala Ala
    130                 135
```

This protein or polypeptide is about 16 kDa and has a pI of 4.45.

Fragments of the above hypersensitive response elicitor polypeptide or protein are encompassed by the present invention.

Suitable fragments can be produced by several means. In the first, subclones of the gene encoding the elicitor protein of the present invention are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-termninal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of SEQ. ID. Nos. 1 and 3, under stringent conditions. An example of suitable high stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 $\mu$m g/ml *E. coli* DNA. However, any DNA molecules hybridizing to a DNA molecule comprising the nucleotide sequences of SEQ. ID. Nos. 1 and 3, under such stringent conditions must not be identical to the nucleic acids encoding the hypersensitive response elicitor proteins or polypeptides of *E. amylovora* (as disclosed by Wei, Z.-M., et al, "Harpin, Elicitor of the Hypersensitive Response Produced by the Plant Pathogen *Erwinia amylovora,*" *Science* 257:85–88 (1992), which is hereby incorporated by reference), Erwinia chrysanthemi (as disclosed by Bauer, et. al., "*Erwinia chrysanthemi* Harpin$_{ECh}$: Soft-Rot Pathogenesis," *MPMI* 8(4): 484–91 (1995), which is hereby incorporated by reference), *Erwinia carotovora* (as disclosed by Cui, et. al., "The RsmA$^-$ Mutants of *Erwinia carotovora* subsp. *carotovora* Strain Ecc71 Overexpress hrpN$_{Ecc}$ and Elicit a Hypersensitive Reaction-like Response in Tobacco Leaves," *MPMI* 9(7): 565–73 (1966), which is hereby incorporated by reference), *Erwinia stewartii* (as disclosed by Ahmad, et. al., "Harpin is not Necessary for the Pathogenicity of *Erwinia stewartii* on Maize," *8th Int'l. Cong. Molec. Plant-Microb. Inter.* Jul. 14–19, 1996 and Ahlnad, et. al., "Harpin is not Necessary for the Pathogenicity of *Erwinia stewartii* on Maize," *Ann. Mtg. Am. Phytopath. Soc.* Jul. 27–31, 1996), which are hereby incorporated by reference), and *Pseudomonas syringae* pv. *syringae* (WO 94/26782 to Cornell Research Foundation, Inc., which is hereby incorporated by reference).

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (MRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promoters. Furthermore, eucaryotic promotors and accompanying genetic signals may not be recognized in or may not function in a procaryotic system, and, further, procaryotic promoters are not recognized and do not function in eucaryotic cells.

Similarly, translation of MRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, Ipp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed.

Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance to plants, enhancing plant growth, and/or effecting insect control for plants. These methods involve applying a hypersensitive response elicitor polypeptide or protein in a non-infectious form to all or part of a plant or a plant seed under conditions where the polypeptide or protein contacts all or part of the cells of the plant or plant seed. Alternatively, the hypersensitive response elicitor protein or polypeptide can be applied to plants such that seeds recovered from such plants themselves are able to impart disease resistance in plants, to enhance plant growth, and/or to effect insect control.

As an alternative to applying a hypersensitive response elicitor polypeptide or protein to plants or plant seeds in order to impart disease resistance in plants, to effect plant growth, and/or to control insects on the plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to impart disease resistance to plants, to enhance plant growth, and/or to control insects. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to impart disease resistance to plants, to enhance plant growth, and/or to control insects.

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptide or protein of the present invention can be isolated from *Erwinia amylovora* as described in the Examples infra. Preferably, however, the isolated hypersensitive response elicitor polypeptide or protein of the present invention is produced recombinantly and purified as described supra.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seed cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli*, which does not elicit a hypersensitive response in plants, can be transformed with genes encoding a hypersensitive response elicitor polypeptide or protein and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato plants or seeds to enhance growth without causing disease in that species.

The method of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana*, Saintpaulia, petunia, pelargonium, poinsettia, chrysanthemum, carnation, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solancearum, Pseudomonas syringae* pv. *tabaci*, and *Xanthamonas campestris* pv. *pelargonii*. Plants can be made resistant, inter alia, to the following fungi by use of the method of the present invention: *Fusarium oxysporum* and *Phytophthora infestans*.

With regard to the use of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds, in accordance with the application embodiment of the present invention, the hypersensitive response elicitor protein or polypeptide can be applied by low or high pressure spraying, coating, immersion, or injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart disease resistance to plants, to enhance plant growth, and/or to control insects on the plants.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art.

The vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, and/or control of insects on the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor to impart disease resistance, enhance growth, and/or control insects. Such plants may also be treated with conventional plant treatment agents (e.g., insecticides, fertilizers, etc.).

Another aspect of the present invention is to utilize the subject elicitor proteins or polypeptides to design molecules that will inactivate, destroy, or bind to these proteins or polypeptides. Since these elicitors are found in plant pathogens, particularly *Erwinia amylovora*, the pathogens themselves can be neutralized by the designed molecules so that disease and/or hypersensitive response is prevented or altered. Examples of disease preventing molecules are antibodies, such as monoclonal or polyclonal antibodies, raised against the elicitor proteins or polypeptides of the present invention or binding portions thereof. Other examples of disease preventing molecules include antibody fragments, half-antibodies, hybrid derivatives, probes, and other molecular constructs.

Monoclonal antibody production may be effected by techniques which are well-known in the art. Basically, the process involves first obtaining immune cells (lymphocytes) from the spleen of a mammal (e.g., mouse) which has been previously immunized, either in vivo or in vitro, with the antigen of interest (e.g., an elicitor protein or polypeptide of the present invention or binding portions thereof). The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the elicitor proteins or polypeptides of the present invention or binding portions thereof. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the elicitor proteins or polypeptides of the present invention or binding portions thereof subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such binding portions include Fab fragments, $F(ab')_2$ fragments, and Fv fragments. These antibody fragments can be made by conventional procedures, such as proteolytic fragmentation procedures, as described in J. Goding, *Monoclonal Antibodies: Principles and Practice*, pp. 98–118 (N.Y. Academic Press 1983), which is hereby incorporated by reference.

Alternatively, the processes of the present invention can utilize probes or ligands found either in nature or prepared synthetically by recombinant DNA procedures or other biological or molecular procedures. Suitable probes or ligands are molecules which bind to the elicitor proteins or polypeptides of the present invention or binding portions thereof.

Avirulence (avr) genes (see Vivian, A., et al, *Microbiology,* 143:693–704 (1997); Leach, J. E., et al., *Annu. Rev. Phytopathol.,* 34:153–179 (1996); Dangl, J. L. "Bacterial Pathogenesis of Plants and Animals: Molecular and Cellular Mechanisms," in *Current Topics in Microbiology and Immunology*, Dangl. J. L., ed. (Springer, Berlin), Vol. 192, pp. 99–118 (1994), which are hereby incorporated by reference) generate signals that trigger defense responses leading to disease resistance in plants with corresponding resistance (R) genes. Typically, avr genes are isolated by expressing a cosmid library from one pathogen in another pathogen and screening for narrowed host range. avr genes traditionally have been considered as negative determinants of host specificity at the race-cultivar level, but some, including the avrE locus from the bacterial speck pathogen *Pseudomonas syringae* pathovar (pv.) tomato (Kobayashi, D. Y., et al., *Proc. Natl. Acad. Sci. USA,* 86:157–61 (1989), which is hereby incorporated by reference), restrict host range at the pathovar-species or species—species level (Whalen, M. C., et al., *Proc. Natl. Acad. Sci. USA,* 85:6743–47 (1988); Swarup, S., et al., *Mol. Plant-Microbe Interact.,* 5:204–13 (1992), which are hereby incorporated by reference). Many avr genes, including avrE, are Hrp regulated. avrE and avrPphE (Mansfield, J., et al., *Mol. Plant-Microbe Interact.,* 7:726–39 (1994), which is hereby incorporated by reference) are physically linked to hrp genes.

When expressed in trans, the avrE locus renderes *P. syringae* pv. glycinea, which causes bacterial blight of soybean, avirulent in all cultivars (Lorang, J. M., et al., *Mol. Plant-Microbe Interact.,* 8:49–57 (1995), which is hereby incorporated by reference). The locus comprises two convergent transcription units, one preceded by a putative $\sigma^{54}$ promoter and the other by a hrp box, a sequence found upstream of many hrp and avr genes that are positively regulated by the alternate sigma factor HrpL (Innes, R. W., et al., *J. Bacteriol.,* 175:4859–69 (1993); Shen, H., et al., *J. Bacterol.,* 175:5916–24 (1993); Xiao, Y., et al., *J. Bacteriol.,* 176:3089–91 (1994), which are hereby incorporated by reference). Expression of both transcripts require HrpL. The avrE locus contributes quantitatively to the virulence in tomato leaves of *P. syringae* pv. tomato strain PT23, but not of strain DC3000 (Lorang, J. M., et al., *Mol. Plant-Microbe Interact.* 8:49–57 (1995); Lorang, J. M., et al., *Mol. Plant-Microbe Interact.* 7:508–515 (1994)).

Thus, avr genes in plant pathogens bind to disease resistance genes in plants which are not susceptible to that pathogen. In view of the homology of the DNA molecules of the present invention to avr genes in plant pathogens, these DNA molecules can be used to identify corresponding plant disease resistance genes. Such identification is carried out by traditional plant breeding techniques in which a pathogen carrying the avr gene is inoculated to plants in screening to track inheritance or identify disruption of the resistance. Once identified, the resistance gene can be isolated by either of two approaches that have proved successful in recent years (see Staskawicz et al., *Science,* 68:661–67 (1995)). These are positional or map-based cloning and insertional mutagenesis or transposon tagging. Because there may be no DspE-insensitive cultivars (susceptible to Pseudomonas harboring dspE; each of four soybean cultivars tested responded to dspE), map-based cloning (which requires crosses between susceptible and resistant lines to identify the position of the resistance gene relative to other genes) may not be feasible. The preferred approach would more likely involve insertional mutagenesis, using the dspE gene or protein in screens to identify lines which had lost the the product of dspE due to transposon tagging of the corresponding resistance gene.

EXAMPLES

Example 1

Recombinant DNA techniques

Isolation of DNA, restriction enzyme digests, ligation, transformation of *Escherichia coli*, and construction of and colony hybridization to screen a *P. syringae* pv. tomato DC3000 genomic library were performed as described by Sambrook, et al. (Sambrook, J., et al., *Molecular cloning: A Laboratory manual*, (Cold Spring Harbor Laboratory, Cold Spring Harbor, N.Y.) (1989), which is hereby incorporated by reference). The library was constructed using pCPP47 (Bauer, D. W., et al., *Mol. Plant-Microbe Interact.,* 10:369–379 (1997), which is hereby incorporated by reference). Except where noted, *E. coli* DH5 and *E. coli* DH5α were used as hosts for DNA clones, and pBluescript or pBC plasmids (Stratagene, La Jolla, Calif.) were used as vectors. *E. amylovora* was transformed by electroporation as described (Bauer, D. W. in "Molecular Genetics of Pathogenicity of *Erwinia amylovora*: Techniques, Tools and Their Applications", (Ph. D. Thesis), Cornell University, Ithaca, N.Y. (1990), which is hereby incorporated by reference). Plasmids were mobilized into *E. amylovora* and *P. syringae* using pRK2013 (Figurski, D., et al., *Proc. Natl. Acad. Sci. USA* 76:1648–1652 (1979), which is hereby incorporated by reference).

Example 2

Nucleotide sequencing and analysis

The nucleotide sequence of the dsp region of *E. amylovora* strain Ea321 was determined using sublcones of pCPP430 (Beer, S. V., et al., in *Advances in Molecular Genetics of Plant-Microbe Interactions*, Hennecke, H., et al., eds. (Kluwer Academic Publishers, Dordrecht, The Netherlands), pp. 53–60 (1991), which is hereby incorporated by reference). The nucleotide sequence of the avrE locus was determined using subclones of pCPP2357, a clone selected from a *P. syringae* pv. tomato DC3000 genomic cosmid library based on hybridization with the hrpRS operon of *P. syringae* pv. syringae, and the finding, based on partial sequencing, that it contained the avrElocus. Nucleotide sequencing was performed by the Cornell Biotechnology Sequencing Facility on a Model 377 Sequencer (Perkin Elmer/Applied Biosystems Division, Foster City, Calif.). Sequence assembly, analysis, and comparisons were performed using the programs of the GCG software package, version 7.1 (Genetics Computer Groups, Inc., Madison, Wis.) and DNASTAR (DNASTAR, Inc., Madison, Wis.). Database searches were performed using BLAST (Altschul, S. F., et al., *Proc. Nat. Acad. Sci. USA,* 87:5509–5513 (1990) which is hereby incorporated by reference).

Example 3

Expression of DspE and DspE' in *E. coli*

The dspE operon was cloned in two pieces into pCPP50, a derivative of $PINIII^{113}$-A2 (Duffaud, G. D., et al. in *Methods in Enzmmology*, Wu, R., et al., eds. (Academic Press, New York), 153:492–50 (1987), which is hereby incorporated by reference) with an expanded polylinker, yielding pCPP1259. Expression in pCPP1259 is driven by the Ipp promoter of *E. coli*, under the control of the lac operator. An intermediate clone, pCPP1244, extending from the start of the operon to the BamHI site in the middle of dspE, also was isolated. *E. coli* DH5α strains containing pCPP1259 and pCPP1244 were grown in LB at 37° C. to an $OD_{620}$ of 0.3. Isopropylthio-β-D-galactoside then was added to 1 mM, and the cells further incubated until reaching an $OD_{620}$ of 0.5. Cells were concentrated two-fold, lysed and subjected to SDS-PAGE as previously described (Sambrook, J., et al., *Molecular cloning: A Laboratory Manual* (Cold Spring Harbor Laboratory, Cold Spring Harbor, N.Y.) (1989), which is hereby incorporated by reference), using 7.5% acrylamide. Cells containing pCPP50 were included for comparison. Proteins were visualized by Coomassie staining.

Example 4

Deletion mutagenesis of dspE 1554 bp were deleted from the 5' HindIII-BamHI fragment of dspE in pCPP1237 using unique StuI and SmaI sites. The mutagenized clone then was inserted into the suicide vector pKNG101 (Kaniga, K., et al., Gene, 109:137–42 (1991), which is hereby incorporated by reference) using *E. coli* SM10λpir as a host, yielding pCPP1241. The mutation, designated Δ1554, then was transferred into *E. amylovora* strains using marker eviction as described previously (Bogdanove, A. J., et al., *J. Bacteriol.,* 178:1720–30 (1996), which is hereby incorporated by reference). 1521 bp were deleted from the 3' HindIII fragment of dspE in pCPP1246 using two BstEII sites blunted with Klenow fragment. This mutation, Δ1521, was transferred into *E. amylovora* strains as above.

Example 5

Pathogenicity assays

For *E. amylovora* strains, cell suspensions of $5\times10^8$ colony-forming units (cfu) per ml were pipetted into wells cut in immature Bartlett pear fruit, or stabbed into Jonamac apple and cotoneaster shoots, and assays carried out as described previously (Beer, S. V., in *Methods in Phytobacteriology*, Klement, Z., et al., eds. (Adadémiai Kiadoó, Budapest), pp. 373–374 (the "1990); Aldwinckle, H. S., et al., *Phytonathology,* 66:1439–44 (1976), which are hereby incorporated by reference). For *P. syringage* pv. glycinea, panels of primary leaves of 2-week-old soybean seedlings (*Glycine max*, cultivar Norchief) were infiltrated with bacterial suspensions of $8\times10^5$ cfu/ml as for the HR assay, below. Plants were then covered with clear plastic bags and incubated under fluorescent lights (16 hr/day) at 22° C. for 5–7 days. Leaves were scored for necrosis and chlorosis.

Example 6

HR assays

Tobacco leaf panels (*Nicotiana tabacum* L. 'xanthi') were infiltrated with bacterial cell suspensions as described previously (Wei, Z. M., et al., *Science,* 257:85–88 (1992); Bauer, D. W., et al., *Mol. Plant-Microbe Interact.,* 4:493–99 (1991), which are hereby incorporated by reference). Primary leaves of 2-week-old soybean seedlings (secondary leaves emerging) were infiltrated with bacterial cell suspensions as for tobacco. Plants were scored for HR (tissue collapse) after 24–48 hr on the laboratory bench. *E. amylovora* strains were suspended in 5 mM $KPO_4$ buffer, pH 6.8, and *P. syringae* strains in 10 mM $MgCl_2$.

Example 7

GUS assays

Cells were 1.) grown in LB to an $OD_{620}$ of 0.9–1.0; 2.) grown in LB to an $OD_{620}$ of 0.5, then washed and resuspended in a hrp-gene-inducing minimal medium (Hrp MM; Huynh, T. V., et al., *Science,* 345:1374–77 (1989), which is hereby incorporated by reference) to an $OD_{620}$ of 0.2 and incubated at 21° C. for 36 hr to a final $OD_{620}$ of 0.9–1.0; or 3.) grown in LB to an $OD_{620}$ of 0.5, washed and concentrated 2-fold in 5 mM $KPO_4$ buffer, pH 6.8, and then transferred to freshly cut wells in pear halves and incubated as for the pathogenicity assay for 36 hr. Cells were assayed for β-glucuronidase (GUS) activity essentially according to Jefferson (Jefferson, R. A., *Plant Molecular Biology Reporter,* 5:387–405 (1987), which is hereby incorporated by reference). For the cells in LB or Hrp MM, 50 μl were mixed with 200 μl GUS extraction buffer (50 mM $NaHPO_4$, pH 7.0, 10 mM β-mercaptoethanol, 10 mM $Na_2EDTA$, 0.1% sodium lauryl sarcosine, 0.1% Triton X-100) containing 2 mM 4-methylumbelliferyl β-D-glucuronide as substrate and incubated at 37° C. for 100 min. For cells in pear fruit, the tissue surrounding the well was excised using a #4 cork borer and homogenized in 5 mM $KPO_4$ buffer, pH 6.8. 200 μl of homogenate was mixed with 800 μl of GUS extraction buffer with substrate and incubated as above. Reactions were stopped by adding $Na_2CO_3$ to a final concentration of 0.2M in a total volume of 2 ml. Fluorescence was measured using a TKO 100 Mini-Fluorometer (Hoefer Scientific Instruments, San Francisco, Calif.). For all samples, cell concentration was estimated by dilution plating, and fluorometric readings were converted to pmole of substrate hydrolyzed/$10^8$ cfu/min, after Miller (Miller, J. H., *A Short Course in Bacterial Genetics: A Laboratory Manual and Handbook for Escherichia coli and Related Bacteria* (Cold Spring Harbor Laboratory Press, Plainview, N.Y.) (1992), which is hereby incorporated by reference).

Example 8

The "disease-specific" (dsp) region of *E. amylovora* consists of a 6.6 kb, two-gene operon.

Mapping of previous transposon insertions (Steinberger, E. M., et al., *Mol. Plant-Microbe Interact.,* 1:135–44 (1988), which is hereby incorporated by reference) that abolish pathogenicity but not HR-eliciting ability confirmed the presence of the "disease specific" (dsp) region downstream of the hrpN gene in strain Ea321 as reported in strain CFBP1430 (Bamy, A. M., et al., *Mol. Microbiol.,* 4:777–86 (1990), which is hereby incorporated by reference). The sequence of approximately 15 kb of DNA downstream of hrpN from Ea321 was determined, revealing several open reading frames (ORFs' FIG. 1). One ORF, in an apparent 6.6 kb operon with a smaller ORF, spanned the area to which the dsp insertions mapped. These two ORFs were designated dspE and dspF. dspE is preceded (beginning 70 bp upstream of the initiation codon) by the sequence $GGAACCN_{15}CAACATAA$ (SEQ. ID. No. 5), which matches the HrpL-dependent promoter consensus sequence or "hrpbox" of *E. amylovora* (Kim, J. H., et al., *J. Bacteriol.,* 179:1690–97 (1997); Kim, J. H., et al., *J. Bacteriol.,* 179:1690–97 (1997), which are hereby incorporated by reference) and strongly resembles the hrp box of *P. syringae* hrp and avr genes (Xiao, Y., et al., *J. Bacteriol.,* 176:3089–91 (1994), which is hereby incorporated by reference). Immediately downstream of dspF is A/T-rich DNA, followed by an ORF (ORF7) highly similar to the *Salmonella typhimurium* gene spvR, a member of the lysR family of regulatory genes (Caldwell, A. L. & Gulig, P. A., *J. Bacteriol,* 173:7176–85 (1991), which is hereby incorporated by reference). Immediately upstream of the dspE operon is a Hrp-regulated gene, hrpW, encoding a novel harpin.

Figure 2:
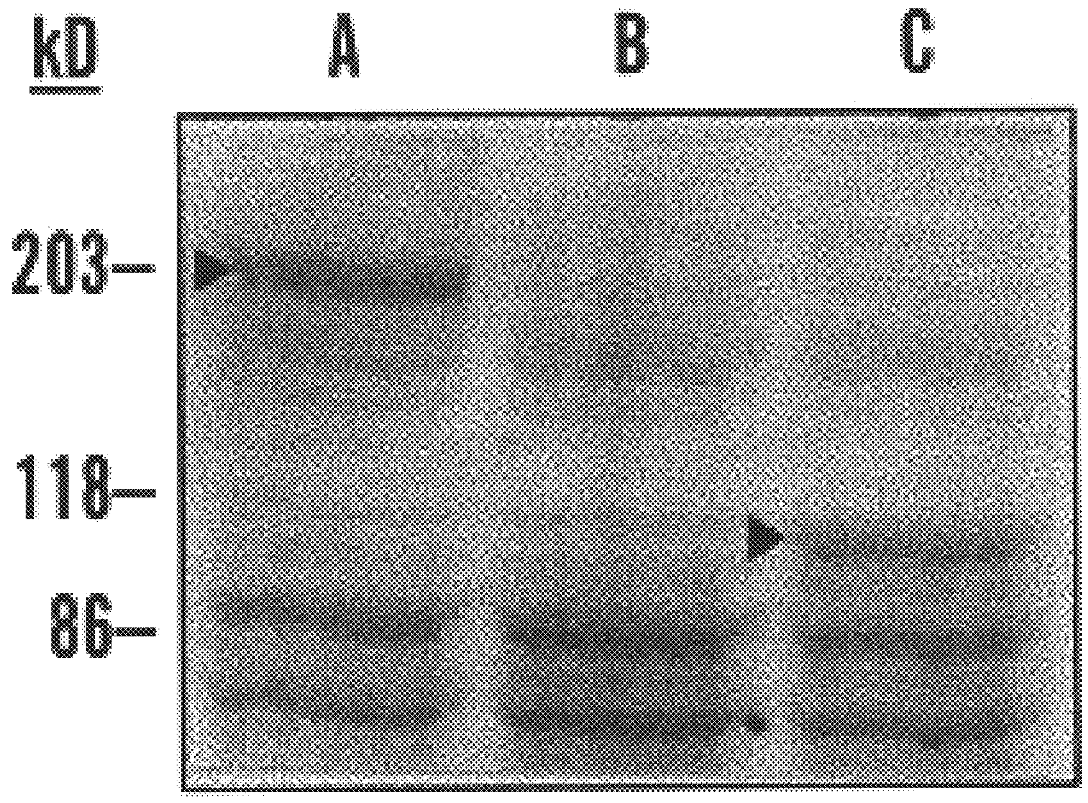
FIG. 2 shows the expression of the full-length and the N-terminal half of DspE in recombinant *E. coli* DH5ax. Lysates of cells carrying either pCPP1259, containing the entire dspE operon (lane A); pCPP50, the cloning vector (lane B); or pCPP1244, containing only the 5' half of the dspE gene (lane C), were subjected to SDS-PAGE followed by Coomassie staining. Bands corresponding to DspE (lane A) and the N-terminal half of DspE (lane C) are marked by arrows. Migration of molecular weight markers is indicated on the left.
Figure 3A:
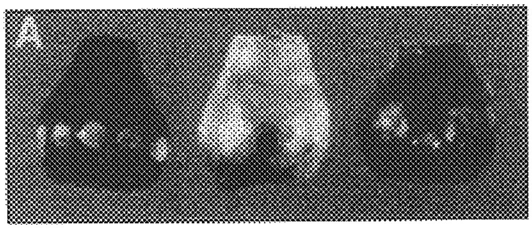
FIGS. 3A–D show the role of dspe in pathogenicity and HR elicitation.
Figure 3B:
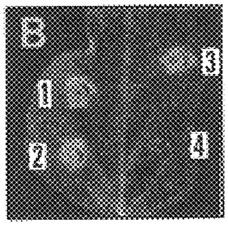
Figure 3C:
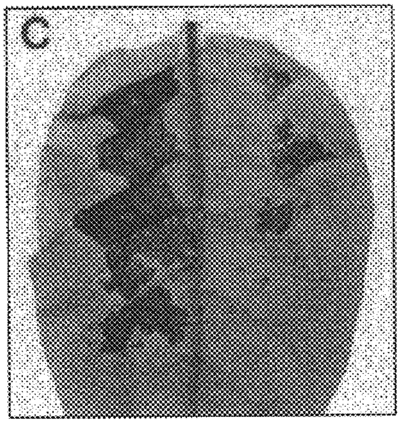
Figure 3D:
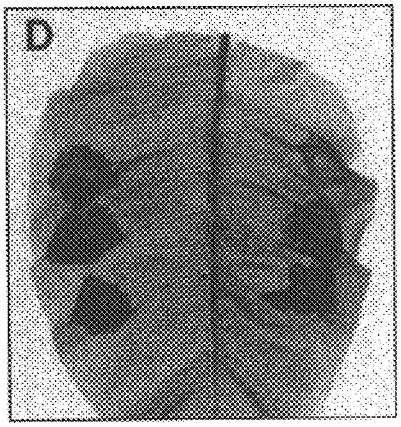

The deduced product of dspE contains 1838 amino acid residues and is hydrophilic. The predicted molecular weight, 198 kD, was confirmed by expression in *E. coli* (FIG. 2). Expression of an intermediate clone containing only the 5' half of dspE yielded a protein of corresponding predicted mobility, suggesting that the N-terminal half of the protein might form an independently stable domain. DspF, predicted to be 16 kD, acidic (pl, 4.45), and predominantly α-helical, with amphipathic α helices in its C-terninus, is physically similar to virulence factor chaperones of animal-pathogenic bacteria (Wattiau, P., et al., *Mol. Microbiol.,* 20:255–62 (1996), which is hereby incorporated by reference).

Example 9 dspE is required for fire blight

Two in-frame deletions within dspE (FIG. 1) were made in Ea321 and Ea273 (low- and high-virulence strains, respectively). The first (Δ1554) corresponds to amino acid residues $G_{203}$ to $G_{720}$, and the second (Δ1521) to amino acid residues $T_{1064}$ to $V_{1570}$. Each deletion abolished the ability of both strains to cause fire blight when inoculated to immature pear fruit (FIG. 3), apple shoots, or cotoneaster shoots. Δ1554 was complemented by a clone carrying only the overlapping 5' half of dspE, further suggesting that the N-terminus of the protein forms a stable domain (FIGS. 1 and 3).

Example 10

The dspe operon contributes quantitatively and in a strain-dependent fashion to HR elicitation by *E. amylovora* in tobacco and is not required for HR elicitation by *E. amylovora* in soybean Transposon insertions in the dsp region reduce the ability of *E. amylovora* to elicit the HR in tobacco (Barny, A. M., et al., *Mol. Microbiol.,* 4:777–86 (1990), which is hereby incorporated by reference). Dilution series of suspensions of dspEΔ1554 mutant strains of Ea321 and Ea273 were infiltrated into tobacco leaves alongside their wild-type parents to assess the role of dspE in HR elicitation (FIG. 3). All strains were capable of eliciting the HR, but Ea321 dspEΔ1554, on a per-cell basis, was roughly one-tenth as effective as the wild-type in eliciting tissue collapse. There was no noticeable difference in HR-eliciting activity, however, between Ea273 and Ea273dspEΔ1554. Ea321dspEΔ1554 elicited wild-type HR in Acme, Centennial, Harasoy, and Norchief soybean leaves (FIG. 3).

Example 11

The dspE operon is Hrp-regulated

Figure 4:
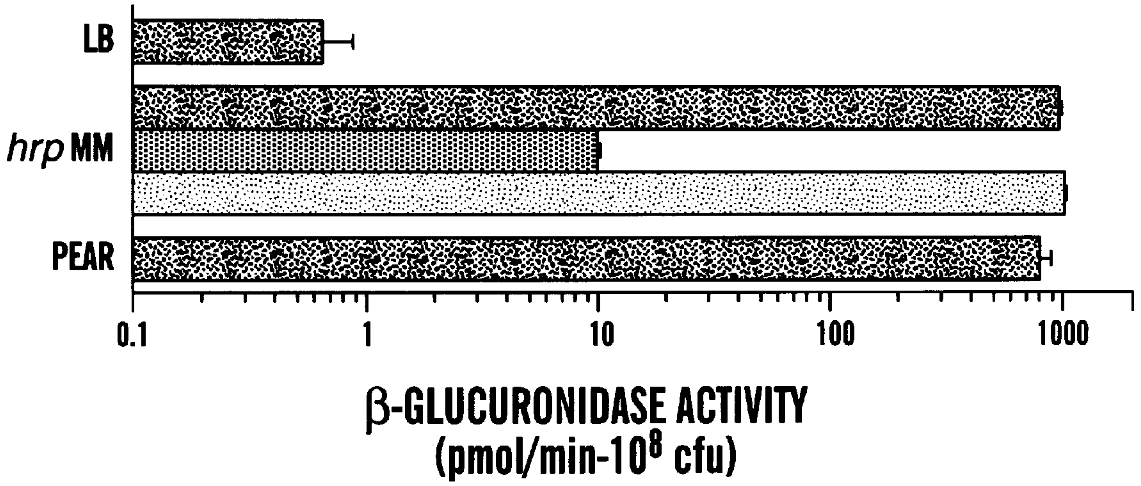
FIG. 4 shows the expression of a promoterless GUS construct fused to dspE in *E. amylovora* Ea273. Ea273 and Ea273dspE::uidA (a merodiploid containing both a wild-type dspE and a truncated dspE fused to the uidA gene; black bars) were grown in LB or Hrp MM, or inoculated to immature pear fruit. Ea273dspE::uidAhrpL::Tn5 (dark gray bar) and Ea273hrcV::Tn5uidA (light gray bar) were also grown in hrp MM. Values shown represent means of triplicate samples normalized for bacterial cell concentration. Standard deviations are represented by lines extending from each bar. The mean values for three samples of Ea273 in each assay were subtracted from, and standard deviations added to, the corresponding values obtained for the other strains.

A promoterless uidA gene construct was cloned downstream of the dspE fragment in pCPP1241 that was used to introduce the Δ1554 mutation (FIG. 1) into wild-type strains of *E. amylovora* (this construct consists of a 3'-truncated dspE gene with the internal deletion). The resulting plasmid, pCPP1263, was mobilized into Ea321 and Ea273. Pathogenic strains, in which plasmid integration had preserved an intact copy of dspE, and non-pathogenic strains, in which the native copy of dspE had been mutated, were isolated. All strains were assayed for GUS activity in Luria Bertani medium (LB) and in Hrp MM, and pathogenic strains were assayed for activity in pear fruit. High levels of activity were obtained from strains incubated in Hrp MM and pear, but not LB. The level of expression in Hrp MM was equivalent to that of a hrcV-uidA fusion ("G73", Wei, et al., *J. Bacteriol.,* 177:6201–10 (1995), which is hereby incorporated by reference) used as a positive control. There were no significant differences in levels of expression of the dspE-uidA fusion in the wild-type and dspE mutant backgrounds, indicating that dspE likely is not autoregulated. Expression of the dspE-uidA fusion in hrpL mutants of Ea321 and Ea273 in hrp MM was two orders of magnitude lower than that in HrpL+strains. Data for Ea273 and derivatives are shown in FIG. 4.

Example 12 dspE and dspF are homologous with genes in the avrE locus of *Pseudomonas syringage* pv. tomato A BLAST (Altschul, S. F., et al., *J. Mol. Biol.,* 215:403–10 (1990), which is hereby incorporated by reference) search of the genetic databases revealed similarity of dspE to a partial sequence of the avrE locus of *P. syringae* pv. tomato (Lorang, J. M., et al., *Mol. Plant-Microbe Interact,* 8:49–57 (1995), which is hereby incorporated by reference). A cosmid library of *P. syringae* pv. tomato DC3000 genomic DNA was constructed, and a clone overlapping the hrp gene cluster and containing the avrE locus was isolated (pCPP2357). The complete nucleotide sequence of the avrE locus was determined, revealing the homolog of dspE (encoding a 195 kD, 1795 amino acid protein of 30% identity) alone in an operon previously designated transcription unit III, and a homolog of dspF (encoding a 14 kD, a 129 amino acid protein of 43% identity) at the end of the juxtaposed and opposing operon previously designated transcription unit IV (FIG. 1). These genes are designated avrE and avrF. The C-terminal half of the DspE and AvrE alignment (from $V_{845}$ of DspE) shows greater conservation (33% identity) than the N-terminal half (26% identity). AvrE contains a motif (aa residues $A_{450}$ to $T_{457}$) conserved in ATP- or GTP-binding proteins ("P-loop"; Saraste, M., et al., *Trends Biochem. Sci.,* 15:430–34 (1990), which is hereby incorporated by reference). This motif is not conserved in DspE, however, and its functional significance in AvrE, if any, is unclear. Amino acid identities are distributed equally throughout the DspF and AvrF alignment, and AvrF shares the predicted physical characteristics of DspF. Upstream of avrF, completing the operon, is a 2.5 kb gene with no similarity to sequences in the genetic databases.

Example 13

The dspE operon functions as an avirulence locus

Figure 5A:
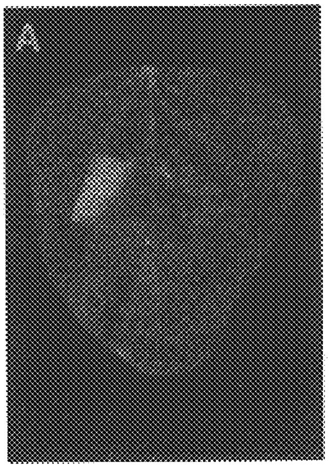
FIGS. 5A–C show the transgeneric avirulence function of the dspE operon and complementation of a dspE mutant with the avrE locus. Norchief soybean leaves were either (See FIG. 5A) infiltrated with $1\times10^{8}$ cfu/ml suspensions of (left) *P. syringae* pv. glycinea race 4 carrying pCPP1250 (containing the dspE operon) or (right) pML 122 (the cloning vector) and photographed after 24 hr at room temperature or (See FIG. 5B) infiltrated with $8\times10^{5}$ cfu/ml suspensions of the same strains and photographed after seven days at 22° C. and high relative humidity. Tissue collapse is apparent on both leaves where the strain carrying pCPP1250 was infiltrated. On the leaf incubated for seven days, chlorosis extending beyond the infiltrated area, typical of disease, is apparent on the half infiltrated with the strain carrying the vector only. The dark section on the side of the leaf infiltrated with the strain carrying pCPP1250 is a shadow caused by a buckle in the leaf.
Figure 5B:
Figure 5C:
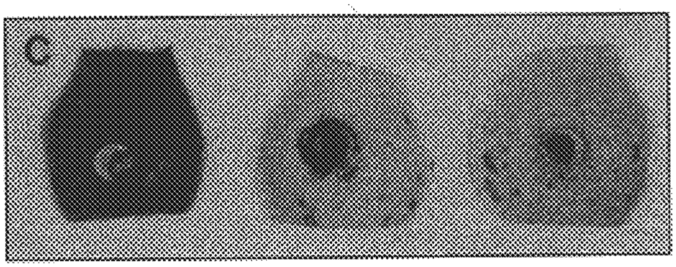

The dspE operon was cloned into pML 122 (Labes, M., et al., *Gene,* 89:37–46 (1990), which is hereby incorporated by reference) downstream of the nptll promoter, and this construct, pCPP1250, was mobilized into *P. syringae* pv. glycinea race 4. The resulting strain, but not a control strain containing pML 122, elicited the HR in soybean cultivars Acme, Centennial, Harasoy, and Norchief; in Norchief plants incubated under conducive conditions, race 4 harboring pCPP1250 failed to cause symptoms of disease, while the control strain caused necrosis and chlorosis that spread from the point of inoculation (FIG. 5).

Example 14 - avrE complements dspE mutations.

Cosmid pCPP2357 was mobilized into Ea321 dspE mutant strains Δ1554 and Δ1521. The resulting transconjugants were pathogenic but low in virulence. Ea321 dspEΔ1521 carrying pCPP2357 with a transposon insertion in the avrE gene was non-pathogenic, demonstrating that the complementation observed was avrE-specific (FIGS. 1 and 5). The same results were observed for transconjugants of the Ea273dspEΔ1521 mutant.

Over thirty bacterial avr genes have been discovered. The plethora of avr genes is thought to result from an "evolutionary tug-of-war" (Dangl, J. L., in *Bacterial Pathogenesis of Plants and Animals: Molecular and Cellular Mechanisms (Current Topics in Microbiology and Immunology*), Dangl. J. L., ed. (Springer, Berlin), 192:99–118 (1994), which is hereby incorporated by reference), a reiterative process of selection, counterselection due to R genes, and modification or substitution of avr genes that was originally discerned by Flor, who hypothesized that "during their parallel evolution host and parasite developed complementary genic systems" (Flor, H. H., *Adv. Genet.,* 8:29–54 (1956), which is hereby incorporated by reference). However, only a few avr genes (including avrE in strain PT23) play detectable roles in virulence or pathogen fitness in their native genetic background (Lorang, J. M., et al., *Mol. Plant-Microbe Interact.,* 7:508–15 (1994); Kearney, B., et al., *Nature,* 346:385–86 (1990); Swarup, S., et al., *Phytopathology,* 81:802–808 (1991); De Feyter, R. D., et al., *Mol. Plant-Microbe Interact.,* 6:225–37 (1993); Ritter, C., et al., *Mol. Plant-Microbe Interact.,* 8:444–53 (1995), which are hereby incorporated by reference), and the selective force driving the maintenance in pathogen genomes of many of these host-range-limiting factors has remained a mystery. It is now clear, though, that several Avr proteins are delivered into plant cells by the Hrp pathway (Gopalan, S., et al., *Plant Celli,* 8:1095–1105 (1996); Tang, X., et al., *Science,* 274:2060–63 (1996); Scofield, S. R., et al., *Science,* 274:2063–65 (1996); Leister, R. T., et al., *Proc. Natl. Acad. Sci. USA,* 93:15497–15502 (1996); Van Den Ackerveken, G., et al., *Cell,* 87:1307–16 (1996), which are hereby incorporated by reference) and, therefore, are likely to be fundamentally virulence factors, which interact (directly, or indirectly through enzymatic products) with host targets to promote parasitism. Mutation of such targets (selected because of reduced susceptibility) as well as the evolution of R proteins that recognize the Avr proteins would force the acquisition or evolution of new or modified Avr proteins and result in the proliferation of avr genes. Cumulatively, these co-evolutionary processes likely would drive a trend toward avr genes with quantitative and redundant effects in pathogenesis rather than critically important roles (Alfano, J. R., et al., *Plant Cell,* 8:1683–16988 (1996), which is hereby incorporated by reference).

It has been found that the homologs dspE and avrE contribute to disease to dramatically different extents. The avirulence locus can substitute transgenerically for the pathogenicity operon, and that the avirulence function of dspE extends across pathogen genera as well. These findings support the hypothesis that avr genes have a primary function in disease. Moreover, they support and expand the coevolutionary model for avr gene proliferation discussed above, and they have practical implications concerning the control of fire blight and other bacterial diseases of perennials.

One can predict from the model that the relative contribution to pathogenicity of a particular factor would reflect, in part, the genetic history of the pathogen, specifically, the degree of co-evolution with its host(s). dspE is required for pathogenicity; avrE has a quantitative, strain-dependent, virulence phenotype. Consistent with the prediction, evolution of corresponding R genes and modification of targets of pathogen virulence factors is likely to have occurred more often and to a greater extent over time in the herbaceous hosts typically infects by *P. syringae* pathovars than in the woody hosts with which *E. amylovora* presumably evolved. Alternatively or additionally, acquisition of dspE (through evolution or horizontal transfer) by *E. amylovora* could have occurred relatively more recently than acquisition of avrE by *P. syringae*, allowing less time for coevolution leading to modification or the development of redundant function.

One could also hypothesize from the model that virulence factors may be conserved among pathogens, yet individually adapted to avoid detection on a particular host. Preliminary results from Southern blot hybridizations suggest that *P. syringae* pv. glycinea harbors an avrE homolog, which, if functional, would support such a hypothesis. Similarly, homologs of the soybean cultivar-specific genes avrA and avrD from *P. syringae* pv. tomato exist in *P. syringae* pv. glycinea (Kobayashi, D. Y., et al., *Proc. Natl. Acad. Sci. USA,* 86:157–161 (1989), which is hereby incorporated by reference).

The homology and abilities of dspE and avrE to function transgenerically expand the model for avr gene proliferation.

Major components of an evolution toward multifactor virulence could be procurement of genes encoding novel virulence factors from heterologus pathogens, and conservation of a functionally cosmopolitan virulence factor delivery system (and possibly conservation of a universal Hrp-pathway-targeting signal on the factors themselves) that would enable their deployment. Indeed, many avr genes are on plasmids and scattered in their distribution among pathogen strains (Dangl, J. L., in *Bacterial Pathogenesis of Plants and Animals: Molecular and Cellular Mechanisms (Current Topics in Microbiology and Immunology)*, Dangl. J. L., ed. (Springer, Berlin), 192:99–118 (1994), which is hereby incorporated by reference), and individual hrp genes are conserved and even interchangeable (Arlat, M., et al., *Mol. Plant-Microbe Interact.,* 4:593–601 (1991); Laby, R. J., et al., *Mol. Plant-Microbe Interact.,* 5:412–19 (1992), which is hereby incorporated by reference). The presence of dspE and avrE in distinct genera suggests horizontal transfer of an ancestral locus, and, although dspE and avrE are homologous and hrp-linked, the transgeneric function of these genes suggests that the Hrp pathways in *E. amylovora* and *P. syringae* have remained insensitive to differences accrued in DspE and AvrE over evolution. It is predicted that even non-homologous Avr-like proteins will function across phytopathogenic bacterial genera.

It remains to be shown whether the avirulence function of the dspE locus is Hrp-pathway-dependent. This seems likely, and it will be important to determine the localization of the dspE and dspF gene products in the plant-bacterial interaction. The physical similarity of DspF (and AvrF) to chaperones required for type III secretion of virulence factors from animal-pathogenic bacteria (Wattiau, P., et al., *Mol. Microbiol.,* 20:255–62 (1996), which is hereby incorporated by reference) is intriguing and novel in phytopathogenic bacteria. The requirement of these chaperones appears to be due to a role other than targeting to the secretion pathway (Woestyn, S., et al., *Mol. Microbiol.,* 20:1261–71 (1996), which is hereby incorporated by reference): chaperones may stabilize proteins, maintain proteins in an appropriate conformation for secretion, or prevent premature polymerization or association with other proteins. Perhaps, DspF binds to DspE (and AvrF to AvrE) and plays a similar role, which might be particularly important for the latter protein due to its large size and probable multidomain nature.

The dspE operon is the first described avirulence locus in *E. amylovora*. A homolog of avrRxv from *Xanthomonas campestris* (Whalen, M. C., et al., *Proc. Natl. Acad. Sci. USA,* 85:6743–47 (1988), which is hereby incorporated by reference) has been found near the dspE operon (Kim, J. F., in *Molecular Characterization of a Novel Harpin and Two hrp Secretory Operons of Erwinia amylovora, and a hrp Operon of E. chrysanthemi* (Ph.D. Thesis), Cornell University, Ithaca, N.Y. (1997)). Monogenic (R-gene-mediated) resistance to fire blight has not been reported, but differential virulence of *E. amyolovora* strains on apple cultivars has been observed (Norelli, J. L., et al., *Phytopathology,* 74:136–39 (1984), which is hereby incorporated by reference). Also, some strains of *E. amylovora* infect Rubus spp. and not pomaceous plants, and vice-versa (Starr, M. P., et al., *Phytopathology,* 41:915–19 (1951), which is hereby incorporated by reference). Whether the dspE operon and the avrRxv homolog or other potential elicitors play a role in these specificities should be determined.

Although the dspE operon triggers defense responses in soybean when expressed in *P. syringae* pv. glycinea, it is not required for the HR of soybean elicited by *E. amylovora*. Neither is hrpN required (FIG. 3). It is possible that *E. amylovora* must have one or the other, dspE or hrpN, to elicit the HR in soybean. It has been observed, however, that purified harpin does not elicit the HR in soybean, suggesting the alternative explanation that *E. amylovora* harbors another avr gene recognized by this plant.

Recognition of *E. amylovora* avirulence signals in soybean indicates the presence of one or more R genes that might be useful for engineering fire blight resistant apple and pear trees. R-gene-mediated resistance to the apple scab pathogen *Venturia inaequalis* (Williams, E. B., et al., *Ann. Rev. Phytopathol.,* 7:223–46 (1969), which is hereby incorporated by reference) and successful transformation of apple with attacin E for control of fire blight (Norelli, J. L., et al., *Euphytica,* 77:123–28 (1994), which is hereby incorporated by reference) attest the feasibility of such an approach. R gene-mediated resistance to apple scab has been overcome in the field (Parisi, L., et al., *Phytopathology,* 83:533–37 (1993), which is hereby incorporated by reference), but the requirement for dspE in disease favors relative durabiliity of a dspE-specific R gene (Kearney, B. et al., *Nature,* 346:385–86 (1990), which is hereby incorporated by reference). Avirulence screening of dspE and other *E. amylovora* genes in pathogens of genetically tractable plants such as Arabidopsis could broaden the pool of candidate R genes and hasten their isolation. A similar approach could be used to isolate R genes effective against other diseases of woody plants. Furthermore, if the dspE operon is as widely conserved as is suggested by its homology with the avrE locus, a corresponding R gene could be effective against a variety of pathogens both of woody and herbaceous plants.

Native (non-denatured) DspE protein has not been produced in sufficient quantity to test its ability to elicit the HR (i.e. hypersensitive response) in a manner similar to hypersensitive response elicitors (i.e., by exogenous application). Therefore, no one has shown that dspE of *E. amylovora* elicits the HR when applied to plants as an isolated cell-free material. However, when the gene encoding the protein is transferred to another bacterium (along with the smaller dspF gene), e.g., *Pseudomonas syringae*, which ordinarily causes disease on certain plants, the recipient bacterium no longer causes disease but instead elicits the HR. The mechanism for this is not known for sure, but it is suspected to involve (and there is compelling evidence for) a mechanism in which the bacterial cell actually injects the DspE protein into the living plant cell, triggering the development of plant cell collapse (i.e. HR). Presumably, when the DspE protein is in the living plant cell, it might signal the plant to develop resistance to insects and pathogens.

Based on the similarity of the predicted physical characteristics of DspF to those of known chaperone proteins from animal pathogens, it is believed that this rather small protein is a chaperone of DspE. Chaperones in animal pathogens bind in the cytoplasm to specific proteins to be secreted. They seem to be required for secretion of the proteins but are not themselves secreted. Evidence suggests that the chaperones are not involved directly in targeting the secreted proteins to the secretion apparatus. Instead, they may act to stabilize the proteins in the cytoplasm and/or prevent their premature aggregation or association with other proteins (e.g., bacterial proteins that direct transport through the host cell-membrane).

The dspE gene bears no similarity to known genes except avrE. Enzymatic function (i.e., one resulting in the production of a secondary molecule that elicits the HR) of DspE cannot be ruled out at present. In fact, one avr gene product is known to elicit HR indirectly by catalyzing synthesis of a diffusible elicitor molecule. However, the simplest explanation for the observed HR eliciting function of the dspE operon expressed in Pseudomonas species is that the protein encoded by the dspE gene is secreted from the bacterium and possibly transported into the plant cell, that there it triggers directly plant defense responses leading to the HR, and that this process is mediated by a specific resistance gene product that recognizes (acts as a receptor of) the DspE protein. Indeed, four avr genes that depend on the Hrp secretory apparatus to function when expressed in bacteria have been shown to cause HR when expressed transgenically within plant cells. One of these has been shown to encode a protein that directly interacts with the product of its corresponding resistance gene. Ultimately, whether DspE elicits plant defense responses from outside or inside the plant cell, directly or through a secondary molecule, must be determined in order to define practical applications of this protein and its encoding gene as a plant defense elicitor.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding a hypersensitive response eliciting protein or polypeptide, wherein the isolated DNA molecule is selected from the group consisting of (a) a DNA molecule comprising a nucleotide sequence of SEQ. ID. Nos. 1 or 3, (b) a DNA molecule encoding a protein comprising an amino acid of SEQ. ID. Nos, 2 or 4, (c) a DNA molecule which hybridizes to a DNA molecule comprising a nucleotide sequence of SEQ. ID Nos. 1 or 3, under stringent conditions comprising hybridization at a temperature of about 65° C. in a hybridization medium comprising about 1M NaCl, and (d) a DNA molecule complementary to DNA molecules (a), (b), and (c).

2. An isolated DNA molecule according to claim 1, wherein said DNA molecule is a DNA molecule comprising a nucleotide sequence of SEQ. ID. Nos. 1 or 3.

3. An isolated DNA molecule according to claim 1, wherein said DNA molecule is a DNA molecule encoding protein comprising an amino acid of SEQ. ID. Nos. 2 or 4.

4. An isolated DNA molecule according to claim 1, wherein said DNA molecule is a DNA molecule which hybridizes to a DNA molecule comprising a nucleotide sequence of SEQ. ID, Nos, 1 or 3, under stringent conditions comprising hybridization at a temperature of about 65° C. in a hybridization medium comprising about 1M NaCl.

5. An isolated DNA molecule according to claim 1, wherein said DNA molecule is a DNA molecule complementary to DNA molecules (a), (b), and (c).

6. An expression vector transformed with the DNA molecule of claim 1.

7. An expression vector according to claim 6, wherein the DNA molecule is in proper sense orientation and correct reading frame.

8. A host cell transformed with the DNA molecule of claim 1.

9. A host cell according to claim 8, wherein the host cell is selected from the group consisting of a plant cell or a bacterial cell.

10. A host cell according to claim 8, wherein the DNA molecule is transformed with an expression vector.

11. A transgenic plant transformed with the DNA molecule of claim 1.

12. A transgenic plant according to claim 11, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

13. A transgenic plant according to claim 11, wherein the plant is selected from the group consisting of *Arabidopsis thaliana*, Saintpaulia, petunia, pelargonium, poinsettia, chrysanthemum, carnation, and zinnia.

14. A transgenic plant seed transformed with the DNA molecule of claim 1.

15. A transgenic plant seed according to claim 14, wherein the plant seed is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

16. A transgenic plant seed according to claim 14, wherein the plant seed is selected from the group consisting of *Arabidopsis thaliana*, Saintpaulia, petunia, pelargonium, poinsettia, chrysanthemum, carnation, and zinnia.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
(A) LENGTH: 5517 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

```
ATGGAATTAA AATCACTGGG AACTGAACAC AAGGCGGCAG TACACACAGC GGCGCACAAC     60
CCTGTGGGGC ATGGTGTTGC CTTACAGCAG GGCAGCAGCA GCAGCAGCCC GCAAAATGCC    120
GCTGCATCAT TGGCGGCAGA AGGCAAAAAT CGTGGGAAAA TGCCGAGAAT TCACCAGCCA    180
TCTACTGCGG CTGATGGTAT CAGCGCTGCT CACCAGCAAA AGAAATCCTT CAGTCTCAGG    240
GGCTGTTTGG GGACGAAAAA ATTTTCCAGA TCGGCACCGC AGGGCCAGCC AGGTACCACC    300
CACAGCAAAG GGGCAACATT GCGCGATCTG CTGGCGCGGG ACGACGGCGA AACGCAGCAT    360
GAGGCGGCCG CGCCAGATGC GGCGCGTTTG ACCCGTTCGG GCGGCGTCAA ACGCCGCAAT    420
ATGGACGACA TGGCCGGGCG GCCAATGGTG AAAGGTGGCA GCGGCGAAGA TAAGGTACCA    480
ACGCAGCAAA AACGGCATCA GCTGAACAAT TTTGGCCAGA TGCGCCAAAC GATGTTGAGC    540
AAAATGGCTC ACCCGGCTTC AGCCAACGCC GGCGATCGCC TGCAGCATTC ACCGCCGCAC    600
ATCCCGGGTA GCCACCACGA AATCAAGGAA GAACCGGTTG GCTCCACCAG CAAGGCAACA    660
ACGGCCCACG CAGACAGAGT GGAAATCGCT CAGGAAGATG ACGACAGCGA ATTCCAGCAA    720
CTGCATCAAC AGCGGCTGGC GCGCGAACGG GAAAATCCAC CGCAGCCGCC CAAACTCGGC    780
GTTGCCACAC CGATTAGCGC CAGGTTTCAG CCCAAACTGA CTGCGGTTGC GGAAAGCGTC    840
CTTGAGGGGA CAGATACCAC GCAGTCACCC CTTAAGCCGC AATCAATGCT GAAAGGAAGT    900
GGAGCCGGGG TAACGCCGCT GGCGGTAACG CTGGATAAAG GCAAGTTGCA GCTGGCACCG    960
GATAATCCAC CCGCGCTCAA TACGTTGTTG AAGCAGACAT TGGGTAAAGA CACCCAGCAC   1020
TATCTGGCGC ACCATGCCAG CAGCGACGGT AGCCAGCATC TGCTGCTGGA CAACAAAGGC   1080
CACCTGTTTG ATATCAAAAG CACCGCCACC AGCTATAGCG TGCTGCACAA CAGCCACCCC   1140
GGTGAGATAA AGGGCAAGCT GGCGCAGGCG GGTACTGGCT CCGTCAGCGT AGACGGTAAA   1200
AGCGGCAAGA TCTCGCTGGG GAGCGGTACG CAAAGTCACA ACAAAACAAT GCTAAGCCAA   1260
```

-continued

```
CCGGGGGAAG CGCACCGTTC CTTATTAACC GGCATTTGGC AGCATCCTGC TGGCGCAGCG   1320
CGGCCGCAGG GCGAGTCAAT CCGCCTGCAT GACGACAAAA TTCATATCCT GCATCCGGAG   1380
CTGGGCGTAT GGCAATCTGC GGATAAAGAT ACCCACAGCC AGCTGTCTCG CCAGGCAGAC   1440
GGTAAGCTCT ATGCGCTGAA AGACAACCGT ACCCTGCAAA ACCTCTCCGA TAATAAATCC   1500
TCAGAAAAGC TGGTCGATAA AATCAAATCG TATTCCGTTG ATCAGCGGGG GCAGGTGGCG   1560
ATCCTGACGG ATACTCCCGG CCGCCATAAG ATGAGTATTA TGCCCTCGCT GGATGCTTCC   1620
CCGGAGAGCC ATATTTCCCT CAGCCTGCAT TTTGCCGATG CCCACCAGGG GTTATTGCAC   1680
GGGAAGTCGG AGCTTGAGGC ACAATCTGTC GCGATCAGCC ATGGGCGACT GGTTGTGGCC   1740
GATAGCGAAG GCAAGCTGTT TAGCGCCGCC ATTCCGAAGC AAGGGGATGG AAACGAACTG   1800
AAAATGAAAG CCATGCCTCA GCATGCGCTC GATGAACATT TTGGTCATGA CCACCAGATT   1860
TCTGGATTTT TCCATGACGA CCACGGCCAG CTTAATGCGC TGGTGAAAAA TAACTTCAGG   1920
CAGCAGCATG CCTGCCCGTT GGGTAACGAT CATCAGTTTC ACCCCGGCTG GAACCTGACT   1980
GATGCGCTGG TTATCGACAA TCAGCTGGGG CTGCATCATA CCAATCCTGA ACCGCATGAG   2040
ATTCTTGATA TGGGGCATTT AGGCAGCCTG GCGTTACAGG AGGGCAAGCT TCACTATTTT   2100
GACCAGCTGA CCAAAGGGTG GACTGGCGCG GAGTCAGATT GTAAGCAGCT GAAAAAAGGC   2160
CTGGATGGAG CAGCTTATCT ACTGAAAGAC GGTGAAGTGA AACGCCTGAA TATTAATCAG   2220
AGCACCTCCT CTATCAAGCA CGGAACGGAA AACGTTTTTT CGCTGCCGCA TGTGCGCAAT   2280
AAACCGGAGC CGGGAGATGC CCTGCAAGGG CTGAATAAAG ACGATAAGGC CCAGGCCATG   2340
GCGGTGATTG GGGTAAATAA ATACCTGGCG CTGACGGAAA AAGGGGACAT TCGCTCCTTC   2400
CAGATAAAAC CCGGCACCCA GCAGTTGGAG CGGCCGGCAC AAACTCTCAG CCGCGAAGGT   2460
ATCAGCGGCG AACTGAAAGA CATTCATGTC GACCACAAGC AGAACCTGTA TGCCTTGACC   2520
CACGAGGGAG AGGTGTTTCA TCAGCCGCGT GAAGCCTGGC AGAATGGTGC CGAAAGCAGC   2580
AGCTGGCACA AACTGGCGTT GCCACAGAGT GAAAGTAAGC TAAAAAGTCT GGACATGAGC   2640
CATGAGCACA AACCGATTGC CACCTTTGAA GACGGTAGCC AGCATCAGCT GAAGGCTGGC   2700
GGCTGGCACG CCTATGCGGC ACCTGAACGC GGGCCGCTGG CGGTGGGTAC CAGCGGTTCA   2760
CAAACCGTCT TTAACCGACT AATGCAGGGG GTGAAAGGCA AGGTGATCCC AGGCAGCGGG   2820
TTGACGGTTA AGCTCTCGGC TCAGACGGGG GGAATGACCG GCGCCGAAGG GCGCAAGGTC   2880
AGCAGTAAAT TTTCCGAAAG GATCCGCGCC TATGCGTTCA ACCCAACAAT GTCCACGCCG   2940
CGACCGATTA AAAATGCTGC TTATGCCACA CAGCACGGCT GGCAGGGGCG TGAGGGGTTG   3000
AAGCCGTTGT ACGAGATGCA GGGAGCGCTG ATTAAACAAC TGGATGCGCA TAACGTTCGT   3060
CATAACGCGC CACAGCCAGA TTTGCAGAGC AAACTGGAAA CTCTGGATTT AGGCGAACAT   3120
GGCGCAGAAT TGCTTAACGA CATGAAGCGC TTCCGCGACG AACTGGAGCA GAGTGCAACC   3180
CGTTCGGTGA CCGTTTTAGG TCAACATCAG GGAGTGCTAA AAAGCAACGG TGAAATCAAT   3240
AGCGAATTTA AGCCATCGCC CGGCAAGGCG TTGGTCCAGA GCTTTAACGT CAATCGCTCT   3300
GGTCAGGATC TAAGCAAGTC ACTGCAACAG GCAGTACATG CCACGCCGCC ATCCGCAGAG   3360
AGTAAACTGC AATCCATGCT GGGGCACTTT GTCAGTGCCG GGGTGGATAT GAGTCATCAG   3420
AAGGGCGAGA TCCCGCTGGG CCGCCAGCGC GATCCGAATG ATAAAACCGC ACTGACCAAA   3480
TCGCGTTTAA TTTTAGATAC CGTGACCATC GGTGAACTGC ATGAACTGGC CGATAAGGCG   3540
AAACTGGTAT CTGACCATAA ACCCGATGCC GATCAGATAA AACAGCTGCG CCAGCAGTTC   3600
GATACGCTGC GTGAAAAGCG GTATGAGAGC AATCCGGTGA AGCATTACAC CGATATGGGC   3660
```

-continued

TTCACCCATA ATAAGGCGCT GGAAGCAAAC TATGATGCGG TCAAAGCCTT TATCAATGCC 3720

TTTAAGAAAG AGCACCACGG CGTCAATCTG ACCACGCGTA CCGTACTGGA ATCACAGGGC 3780

AGTGCGGAGC TGGCGAAGAA GCTCAAGAAT ACGCTGTTGT CCCTGGACAG TGGTGAAAGT 3840

ATGAGCTTCA GCCGGTCATA TGGCGGGGGC GTCAGCACTG TCTTTGTGCC TACCCTTAGC 3900

AAGAAGGTGC CAGTTCCGGT GATCCCCGGA GCCGGCATCA CGCTGGATCG CGCCTATAAC 3960

CTGAGCTTCA GTCGTACCAG CGGCGGATTG AACGTCAGTT TTGGCCGCGA CGGCGGGGTG 4020

AGTGGTAACA TCATGGTCGC TACCGGCCAT GATGTGATGC CCTATATGAC CGGTAAGAAA 4080

ACCAGTGCAG GTAACGCCAG TGACTGGTTG AGCGCAAAAC ATAAAATCAG CCCGGACTTG 4140

CGTATCGGCG CTGCTGTGAG TGGCACCCTG CAAGGAACGC TACAAAACAG CCTGAAGTTT 4200

AAGCTGACAG AGGATGAGCT GCCTGGCTTT ATCCATGGCT TGACGCATGG CACGTTGACC 4260

CCGGCAGAAC TGTTGCAAAA GGGGATCGAA CATCAGATGA AGCAGGGCAG CAAACTGACG 4320

TTTAGCGTCG ATACCTCGGC AAATCTGGAT CTGCGTGCCG GTATCAATCT GAACGAAGAC 4380

GGCAGTAAAC CAAATGGTGT CACTGCCCGT GTTTCTGCCG GCTAAGTGC ATCGGCAAAC 4440

CTGGCCGCCG GCTCGCGTGA ACGCAGCACC ACCTCTGGCC AGTTTGGCAG CACGACTTCG 4500

GCCAGCAATA ACCGCCCAAC CTTCCTCAAC GGGGTCGGCG CGGGTGCTAA CCTGACGGCT 4560

GCTTTAGGGG TTGCCCATTC ATCTACGCAT GAAGGGAAAC CGGTCGGGAT CTTCCCGGCA 4620

TTTACCTCGA CCAATGTTTC GGCAGCGCTG GCGCTGGATA ACCGTACCTC ACAGAGTATC 4680

AGCCTGGAAT TGAAGCGCGC GGAGCCGGTG ACCAGCAACG ATATCAGCGA GTTGACCTCC 4740

ACGCTGGGAA AACACTTTAA GGATAGCGCC ACAACGAAGA TGCTTGCCGC TCTCAAAGAG 4800

TTAGATGACG CTAAGCCCGC TGAACAACTG CATATTTTAC AGCAGCATTT CAGTGCAAAA 4860

GATGTCGTCG GTGATGAACG CTACGAGGCG GTGCGCAACC TGAAAAAACT GGTGATACGT 4920

CAACAGGCTG CGGACAGCCA CAGCATGGAA TTAGGATCTG CCAGTCACAG CACGACCTAC 4980

AATAATCTGT CGAGAATAAA TAATGACGGC ATTGTCGAGC TGCTACACAA ACATTTCGAT 5040

GCGGCATTAC CAGCAAGCAG TGCCAAACGT CTTGGTGAAA TGATGAATAA CGATCCGGCA 5100

CTGAAAGATA TTATTAAGCA GCTGCAAAGT ACGCCGTTCA GCAGCGCCAG CGTGTCGATG 5160

GAGCTGAAAG ATGGTCTGCG TGAGCAGACG GAAAAAGCAA TACTGGACGG TAAGGTCGGT 5220

CGTGAAGAAG TGGGAGTACT TTTCCAGGAT CGTAACAACT TGCGTGTTAA ATCGGTCAGC 5280

GTCAGTCAGT CCGTCAGCAA AAGCGAAGGC TTCAATACCC CAGCGCTGTT ACTGGGGACG 5340

AGCAACAGCG CTGCTATGAG CATGGAGCGC AACATCGGAA CCATTAATTT TAAATACGGC 5400

CAGGATCAGA ACACCCCACG GCGATTTACC CTGGAGGGTG GAATAGCTCA GGCTAATCCG 5460

CAGGTCGCAT CTGCGCTTAC TGATTTGAAG AAGGAAGGGC TGGAAATGAA GAGCTAA 5517

(2) INFORMATION FOR SEQ ID NO:2:

(i) SEQUENCE CHARACTERISTICS:
(A) LENGTH: 1838 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:2:

Met Glu Leu Lys Ser Leu Gly Thr Glu His Lys Ala Ala Val His Thr
1 5 10 15

-continued

```
Ala Ala His Asn Pro Val Gly His Gly Val Ala Leu Gln Gln Gly Ser
            20                  25                  30

Ser Ser Ser Ser Pro Gln Asn Ala Ala Ala Ser Leu Ala Ala Glu Gly
        35                  40                  45

Lys Asn Arg Gly Lys Met Pro Arg Ile His Gln Pro Ser Thr Ala Ala
    50                  55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
    210                 215                 220

Asp Arg Val Glu Ile Ala Gln Glu Asp Asp Asp Ser Glu Phe Gln Gln
225                 230                 235                 240

Leu His Gln Gln Arg Leu Ala Arg Glu Arg Glu Asn Pro Pro Gln Pro
                245                 250                 255

Pro Lys Leu Gly Val Ala Thr Pro Ile Ser Ala Arg Phe Gln Pro Lys
            260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
    290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
            340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
    370                 375                 380

Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
                405                 410                 415

Met Leu Ser Gln Pro Gly Glu Ala His Arg Ser Leu Leu Thr Gly Ile
            420                 425                 430

Trp Gln His Pro Ala Gly Ala Ala Arg Pro Gln Gly Glu Ser Ile Arg
```

-continued

```
        435                 440                 445

Leu His Asp Asp Lys Ile His Ile Leu His Pro Glu Leu Gly Val Trp
    450                 455                 460

Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
        515                 520                 525

His Lys Met Ser Ile Met Pro Ser Leu Asp Ala Ser Pro Glu Ser His
    530                 535                 540

Ile Ser Leu Ser Leu His Phe Ala Asp Ala His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
        595                 600                 605

Ala Leu Asp Glu His Phe Gly His Asp His Gln Ile Ser Gly Phe Phe
    610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Glu Pro His Glu Ile Leu Asp Met Gly His Leu Gly
        675                 680                 685

Ser Leu Ala Leu Gln Glu Gly Lys Leu His Tyr Phe Asp Gln Leu Thr
    690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
                725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
        755                 760                 765

Gln Gly Leu Asn Lys Asp Asp Lys Ala Gln Ala Met Ala Val Ile Gly
    770                 775                 780

Val Asn Lys Tyr Leu Ala Leu Thr Glu Lys Gly Asp Ile Arg Ser Phe
785                 790                 795                 800

Gln Ile Lys Pro Gly Thr Gln Gln Leu Glu Arg Pro Ala Gln Thr Leu
                805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
        835                 840                 845

Pro Arg Glu Ala Trp Gln Asn Gly Ala Glu Ser Ser Ser Trp His Lys
    850                 855                 860
```

-continued

```
Leu Ala Leu Pro Gln Ser Glu Ser Lys Leu Lys Ser Leu Asp Met Ser
865                 870                 875                 880

His Glu His Lys Pro Ile Ala Thr Phe Glu Asp Gly Ser Gln His Gln
                885                 890                 895

Leu Lys Ala Gly Gly Trp His Ala Tyr Ala Ala Pro Glu Arg Gly Pro
            900                 905                 910

Leu Ala Val Gly Thr Ser Gly Ser Gln Thr Val Phe Asn Arg Leu Met
        915                 920                 925

Gln Gly Val Lys Gly Lys Val Ile Pro Gly Ser Gly Leu Thr Val Lys
    930                 935                 940

Leu Ser Ala Gln Thr Gly Gly Met Thr Gly Ala Glu Gly Arg Lys Val
945                 950                 955                 960

Ser Ser Lys Phe Ser Glu Arg Ile Arg Ala Tyr Ala Phe Asn Pro Thr
                965                 970                 975

Met Ser Thr Pro Arg Pro Ile Lys Asn Ala Ala Tyr Ala Thr Gln His
            980                 985                 990

Gly Trp Gln Gly Arg Glu Gly Leu Lys Pro Leu Tyr Glu Met Gln Gly
        995                 1000                1005

Ala Leu Ile Lys Gln Leu Asp Ala His Asn Val Arg His Asn Ala Pro
    1010                1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
                1045                1050                1055

Gln Ser Ala Thr Arg Ser Val Thr Val Leu Gly Gln His Gln Gly Val
            1060                1065                1070

Leu Lys Ser Asn Gly Glu Ile Asn Ser Glu Phe Lys Pro Ser Pro Gly
        1075                1080                1085

Lys Ala Leu Val Gln Ser Phe Asn Val Asn Arg Ser Gly Gln Asp Leu
    1090                1095                1100

Ser Lys Ser Leu Gln Gln Ala Val His Ala Thr Pro Pro Ser Ala Glu
1105                1110                1115                1120

Ser Lys Leu Gln Ser Met Leu Gly His Phe Val Ser Ala Gly Val Asp
                1125                1130                1135

Met Ser His Gln Lys Gly Glu Ile Pro Leu Gly Arg Gln Arg Asp Pro
            1140                1145                1150

Asn Asp Lys Thr Ala Leu Thr Lys Ser Arg Leu Ile Leu Asp Thr Val
        1155                1160                1165

Thr Ile Gly Glu Leu His Glu Leu Ala Asp Lys Ala Lys Leu Val Ser
    1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
                1205                1210                1215

Thr Asp Met Gly Phe Thr His Asn Lys Ala Leu Glu Ala Asn Tyr Asp
            1220                1225                1230

Ala Val Lys Ala Phe Ile Asn Ala Phe Lys Lys Glu His His Gly Val
        1235                1240                1245

Asn Leu Thr Thr Arg Thr Val Leu Glu Ser Gln Gly Ser Ala Glu Leu
    1250                1255                1260

Ala Lys Lys Leu Lys Asn Thr Leu Leu Ser Leu Asp Ser Gly Glu Ser
1265                1270                1275                1280
```

-continued

```
Met Ser Phe Ser Arg Ser Tyr Gly Gly Gly Val Ser Thr Val Phe Val
                1285                1290                1295

Pro Thr Leu Ser Lys Lys Val Pro Val Pro Val Ile Pro Gly Ala Gly
            1300                1305                1310

Ile Thr Leu Asp Arg Ala Tyr Asn Leu Ser Phe Ser Arg Thr Ser Gly
        1315                1320                1325

Gly Leu Asn Val Ser Phe Gly Arg Asp Gly Gly Val Ser Gly Asn Ile
    1330                1335                1340

Met Val Ala Thr Gly His Asp Val Met Pro Tyr Met Thr Gly Lys Lys
1345                1350                1355                1360

Thr Ser Ala Gly Asn Ala Ser Asp Trp Leu Ser Ala Lys His Lys Ile
                1365                1370                1375

Ser Pro Asp Leu Arg Ile Gly Ala Ala Val Ser Gly Thr Leu Gln Gly
            1380                1385                1390

Thr Leu Gln Asn Ser Leu Lys Phe Lys Leu Thr Glu Asp Glu Leu Pro
        1395                1400                1405

Gly Phe Ile His Gly Leu Thr His Gly Thr Leu Thr Pro Ala Glu Leu
    1410                1415                1420

Leu Gln Lys Gly Ile Glu His Gln Met Lys Gln Gly Ser Lys Leu Thr
1425                1430                1435                1440

Phe Ser Val Asp Thr Ser Ala Asn Leu Asp Leu Arg Ala Gly Ile Asn
                1445                1450                1455

Leu Asn Glu Asp Gly Ser Lys Pro Asn Gly Val Thr Ala Arg Val Ser
            1460                1465                1470

Ala Gly Leu Ser Ala Ser Ala Asn Leu Ala Ala Gly Ser Arg Glu Arg
        1475                1480                1485

Ser Thr Thr Ser Gly Gln Phe Gly Ser Thr Thr Ser Ala Ser Asn Asn
    1490                1495                1500

Arg Pro Thr Phe Leu Asn Gly Val Gly Ala Gly Ala Asn Leu Thr Ala
1505                1510                1515                1520

Ala Leu Gly Val Ala His Ser Ser Thr His Glu Gly Lys Pro Val Gly
                1525                1530                1535

Ile Phe Pro Ala Phe Thr Ser Thr Asn Val Ser Ala Ala Leu Ala Leu
            1540                1545                1550

Asp Asn Arg Thr Ser Gln Ser Ile Ser Leu Glu Leu Lys Arg Ala Glu
        1555                1560                1565

Pro Val Thr Ser Asn Asp Ile Ser Glu Leu Thr Ser Thr Leu Gly Lys
    1570                1575                1580

His Phe Lys Asp Ser Ala Thr Thr Lys Met Leu Ala Ala Leu Lys Glu
1585                1590                1595                1600

Leu Asp Asp Ala Lys Pro Ala Glu Gln Leu His Ile Leu Gln Gln His
                1605                1610                1615

Phe Ser Ala Lys Asp Val Val Gly Asp Glu Arg Tyr Glu Ala Val Arg
            1620                1625                1630

Asn Leu Lys Lys Leu Val Ile Arg Gln Gln Ala Ala Asp Ser His Ser
        1635                1640                1645

Met Glu Leu Gly Ser Ala Ser His Ser Thr Thr Tyr Asn Asn Leu Ser
    1650                1655                1660

Arg Ile Asn Asn Asp Gly Ile Val Glu Leu Leu His Lys His Phe Asp
1665                1670                1675                1680

Ala Ala Leu Pro Ala Ser Ser Ala Lys Arg Leu Gly Glu Met Met Asn
                1685                1690                1695

Asn Asp Pro Ala Leu Lys Asp Ile Ile Lys Gln Leu Gln Ser Thr Pro
```

-continued

```
            1700                1705                1710

Phe Ser Ser Ala Ser Val Ser Met Glu Leu Lys Asp Gly Leu Arg Glu
        1715                1720                1725

Gln Thr Glu Lys Ala Ile Leu Asp Gly Lys Val Gly Arg Glu Glu Val
    1730                1735                1740

Gly Val Leu Phe Gln Asp Arg Asn Asn Leu Arg Val Lys Ser Val Ser
1745                1750                1755                1760

Val Ser Gln Ser Val Ser Lys Ser Glu Gly Phe Asn Thr Pro Ala Leu
                1765                1770                1775

Leu Leu Gly Thr Ser Asn Ser Ala Ala Met Ser Met Glu Arg Asn Ile
            1780                1785                1790

Gly Thr Ile Asn Phe Lys Tyr Gly Gln Asp Gln Asn Thr Pro Arg Arg
        1795                1800                1805

Phe Thr Leu Glu Gly Gly Ile Ala Gln Ala Asn Pro Gln Val Ala Ser
    1810                1815                1820

Ala Leu Thr Asp Leu Lys Lys Glu Gly Leu Glu Met Lys Ser
1825                1830                1835
```

(2) INFORMATION FOR SEQ ID NO:3:

(i) SEQUENCE CHARACTERISTICS:
(A) LENGTH: 420 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

```
ATGACATCGT CACAGCAGCG GGTTGAAAGG TTTTTACAGT ATTTCTCCGC CGGGTGTAAA      60

ACGCCCATAC ATCTGAAAGA CGGGGTGTGC GCCCTGTATA ACGAACAAGA TGAGGAGGCG     120

GCGGTGCTGG AAGTACCGCA ACACAGCGAC AGCCTGTTAC TACACTGCCG AATCATTGAG     180

GCTGACCCAC AAACTTCAAT AACCCTGTAT TCGATGCTAT TACAGCTGAA TTTTGAAATG     240

GCGGCCATGC GCGGCTGTTG GCTGGCGCTG GATGAACTGC ACAACGTGCG TTTATGTTTT     300

CAGCAGTCGC TGGAGCATCT GGATGAAGCA AGTTTTAGCG ATATCGTTAG CGGCTTCATC     360

GAACATGCGG CAGAAGTGCG TGAGTATATA GCGCAATTAG ACGAGAGTAG CGCGGCATAA     420
```

(2) INFORMATION FOR SEQ ID NO:4:

(i) SEQUENCE CHARACTERISTICS:
(A) LENGTH: 139 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

```
Met Thr Ser Ser Gln Gln Arg Val Glu Arg Phe Leu Gln Tyr Phe Ser
1               5                   10                  15

Ala Gly Cys Lys Thr Pro Ile His Leu Lys Asp Gly Val Cys Ala Leu
            20                  25                  30

Tyr Asn Glu Gln Asp Glu Glu Ala Ala Val Leu Glu Val Pro Gln His
        35                  40                  45

Ser Asp Ser Leu Leu Leu His Cys Arg Ile Ile Glu Ala Asp Pro Gln
    50                  55                  60

Thr Ser Ile Thr Leu Tyr Ser Met Leu Leu Gln Leu Asn Phe Glu Met
```

-continued

```
65                  70                  75                  80

Ala Ala Met Arg Gly Cys Trp Leu Ala Leu Asp Glu Leu His Asn Val
                85                  90                  95

Arg Leu Cys Phe Gln Gln Ser Leu Glu His Leu Asp Glu Ala Ser Phe
            100                 105                 110

Ser Asp Ile Val Ser Gly Phe Ile Glu His Ala Ala Glu Val Arg Glu
        115                 120                 125

Tyr Ile Ala Gln Leu Asp Glu Ser Ser Ala Ala
    130                 135


(2) INFORMATION FOR SEQ ID NO:5:

     (i) SEQUENCE CHARACTERISTICS:
          (A) LENGTH: 29 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:5:

GGAACCNNNN NNNNNNNNNN NCAACATAA                                    29
```